United States Patent [19]
Larsen et al.

[11] Patent Number: 5,782,832
[45] Date of Patent: Jul. 21, 1998

[54] SPINAL FUSION IMPLANT AND METHOD OF INSERTION THEREOF

[75] Inventors: Scott W. Larsen, Newtown; Oleg Shikhman, Fairfield, both of Conn.

[73] Assignee: Surgical Dynamics, Inc., Norwalk, Conn.

[21] Appl. No.: 725,666

[22] Filed: Oct. 1, 1996

[51] Int. Cl.$^6$ ............................................. A61B 17/56
[52] U.S. Cl. ................................................ 606/61; 623/17
[58] Field of Search .................................. 606/61; 623/17

[56] References Cited

U.S. PATENT DOCUMENTS

| | | |
|---|---|---|
| 3,486,505 | 12/1969 | Morrison . |
| 3,719,186 | 3/1973 | Merig, Jr. . |
| 3,848,601 | 11/1974 | Ma et al. . |

(List continued on next page.)

FOREIGN PATENT DOCUMENTS

| | | | |
|---|---|---|---|
| 0307241 | 3/1989 | European Pat. Off. . | |
| 0551187 | 7/1993 | European Pat. Off. . | |
| 610837 | 8/1994 | European Pat. Off. | ............ 623/17 |
| 0716840 | 6/1996 | European Pat. Off. . | |
| 0732093 | 9/1996 | European Pat. Off. . | |
| 0734703 | 10/1996 | European Pat. Off. . | |
| 2295729 | 12/1974 | France . | |
| 2350824 | 3/1977 | France . | |
| 2710519 | 9/1993 | France . | |
| 1961531 | 12/1969 | Germany . | |
| 3505567 | 2/1985 | Germany . | |
| 4302397 | 1/1993 | Germany . | |
| 4323595 | 7/1993 | Germany . | |
| 5729348 | 2/1982 | Japan . | |
| 58-78653 | 5/1983 | Japan . | |
| 61-135652 | 6/1986 | Japan . | |
| 62-164458 | 7/1987 | Japan . | |
| 63-43654 | 2/1988 | Japan . | |
| 1502402 | 8/1989 | Japan . | |
| 1314560 | 12/1989 | Japan . | |
| 8707827 | 12/1987 | WIPO . | |
| 8912431 | 12/1989 | WIPO . | |
| 9106261 | 5/1991 | WIPO . | |
| 9404100 | 3/1994 | WIPO | ............ 623/17 |
| 9417759 | 8/1994 | WIPO . | |
| 9608205 | 3/1996 | WIPO . | |

OTHER PUBLICATIONS

Jose M. Otero Vich, "Anterior Cervical Interbody Fusion With Threaded Cylindrical Bone", *J. Neurosurg.*, 63:750–753, 1985.

Norman W. Hoover, "Methods of Lumbar Fusion", *The Journal of Bone and Joint Surgery*, vol. 50-A, No. 1, Jan. 1968, pp. 194–210.

Benjamin R. Wiltberger, "Intervertebral Body Fusion By the Use of Posterior Bone Dowel", pp. 69–79.

Parviz Kambin et al., "Percutaneous Lateral Discectomy of the Lumbar Spine", *Clinical Orthopaedics*, Apr. 1983, vol. 174, pp. 127–131.

Guy M. Sava et al., "Posterior Lumbar Interbody Fusion Made Simple", Neurological Surgery Associates of Cincinnati, Inc. Cage CH: Lumbar Spacing Cages, *Scientix*.

Actualities Vertebrales, La Herni Discale Cervicale, No. 2, Avril 1994, pp. 1–11.

(List continued on next page.)

*Primary Examiner*—Michael Powell Buiz
*Assistant Examiner*—Julian W. Woo

[57] ABSTRACT

A spinal fusion implant includes lower and upper plate members dimensioned for at least partial insertion within the intervertebral space defined between adjacent vertebrae. The lower and upper plate members have contacting surfaces for engaging respective vertebral end faces of the adjacent vertebrae. A linkage mechanism including at least one link member operatively connects the lower and upper plate members. The linkage mechanism actuable to cause relative movement of the lower and upper plate members, wherein upon actuation, the contacting surfaces of the lower and upper plate members engage the vertebral end faces with the lower and upper plate members supporting the adjacent vertebrae in spaced relation during healing.

18 Claims, 17 Drawing Sheets

U.S. PATENT DOCUMENTS

| | | |
|---|---|---|
| 3,905,047 | 9/1975 | Long . |
| 3,916,907 | 11/1975 | Peterson . |
| 4,177,524 | 12/1979 | Grell et al. . |
| 4,484,570 | 11/1984 | Sutter et al. . |
| 4,501,269 | 2/1985 | Bagby . |
| 4,537,185 | 8/1985 | Stednitz . |
| 4,545,374 | 10/1985 | Jacobson . |
| 4,573,448 | 3/1986 | Kambin . |
| 4,677,972 | 7/1987 | Tornier . |
| 4,743,256 | 5/1988 | Brantigan . |
| 4,772,287 | 9/1988 | Ray et al. . |
| 4,820,305 | 4/1989 | Harms et al. . |
| 4,834,757 | 5/1989 | Brantigan . |
| 4,863,476 | 9/1989 | Shepperd . |
| 4,874,389 | 10/1989 | Downey . |
| 4,877,020 | 10/1989 | Vich . |
| 4,878,915 | 11/1989 | Brantigan . |
| 4,927,421 | 5/1990 | Goble et al. . |
| 4,936,848 | 6/1990 | Bagby . |
| 4,950,270 | 8/1990 | Bowman et al. . |
| 4,961,740 | 10/1990 | Ray et al. . |
| 5,015,247 | 5/1991 | Michelson . |
| 5,015,255 | 5/1991 | Kuslich . |
| 5,026,373 | 6/1991 | Ray et al. . |
| 5,055,104 | 10/1991 | Ray . |
| 5,059,193 | 10/1991 | Kuslich . |
| 5,062,845 | 11/1991 | Kuslich et al. . |
| 5,064,425 | 11/1991 | Branemark et al. . |
| 5,139,499 | 8/1992 | Small et al. . |
| 5,147,402 | 9/1992 | Bohler et al. . |
| 5,171,278 | 12/1992 | Pisharodi . |
| 5,192,327 | 3/1993 | Brantigan . |
| 5,195,541 | 3/1993 | Obenchain . |
| 5,258,031 | 11/1993 | Salib et al. ............... 606/61 |
| 5,263,953 | 11/1993 | Bagby . |
| 5,300,076 | 4/1994 | Leriche . |
| 5,306,310 | 4/1994 | Siebels . |
| 5,313,962 | 5/1994 | Obenchain . |
| 5,354,302 | 10/1994 | Ko . |
| 5,357,983 | 10/1994 | Mathews . |
| 5,390,683 | 2/1995 | Pisharodi . |
| 5,395,317 | 3/1995 | Kambin . |
| 5,423,816 | 6/1995 | Lin . |
| 5,423,817 | 6/1995 | Lin . |
| 5,425,772 | 6/1995 | Brantigan . |
| 5,431,658 | 7/1995 | Moskovich . |
| 5,439,464 | 8/1995 | Shapiro . |
| 5,443,514 | 8/1995 | Steffee . |
| 5,443,515 | 8/1995 | Cohen et al. . |
| 5,445,639 | 8/1995 | Kuslich et al. . |
| 5,458,638 | 10/1995 | Kuslich et al. . |
| 5,484,437 | 1/1996 | Michelson . |
| 5,489,307 | 2/1996 | Kuslich et al. . |
| 5,489,308 | 2/1996 | Kuslich et al. . |
| 5,505,732 | 4/1996 | Michelson . |
| 5,507,816 | 4/1996 | Bullivant ............... 623/17 |
| 5,522,899 | 6/1996 | Michelson . |
| 5,534,031 | 7/1996 | Matsuzaki et al. . |
| 5,554,191 | 9/1996 | Lahille et al. . |
| 5,562,736 | 10/1996 | Ray et al. . |
| 5,571,109 | 11/1996 | Bertagnoli . |
| 5,571,189 | 11/1996 | Kuslich . |
| 5,571,192 | 11/1996 | Schönhöffer . |
| 5,609,635 | 3/1997 | Michelson ............... 606/61 |

OTHER PUBLICATIONS

Kiyoshi Kaneda and Isao Yamamoto, "Spinal Instrumentation Surgery In Lumbar and Lumbosacral Spine," *The Improvement of Medicine*, vol. 147, No. 14, Dec. 31, 1988.

Hiroshi Yamamoto, "Spinal Instrumentation For Lumbar Spine Segmental Transverse Wiring For Spondylolysis and Pedicular Screw–Spinal Plate For Spondylolisthesis," *The Improvement of Medicine*, vol. 145, No. 1, Apr. 2, 1988.

Kenichiro Shibata, Masayoshi Oga, Kazuo Hayashi, Yoichi Sugioka, "A New Contrivance of Anterior Spinal Fusion in Cervical Spine", *Orthopaedic and Traumatic Surgery*, vol. 35, No. 3, pp. 811–813, 1987.

Haruo Tsuji, "Anterior Body Fusion of Lumbar Spine Hernia," *Operation*, vol. 41, No. 11, pp. 1803–1811, 1987.

Hirotugu Oda, Shinya Kawai, Tetsuro Murakami, et al., "Osteoplastic Hemi/Bilateral Partial Laminectomy of Lumbar Spinal Hernia," *Operation*, vol. 41, No. 11, pp. 1785–1791, 1987.

Teiji Yano, et al., "Treatment of Spondylolisthesis By Posterior Fusion With Bone Grafting To Neutral Arch Defect," *Clinical Orthopaedic Surgery*, vol. 17, No. 4, pp. 394–399, 1982.

Toshihiko Yamane, et al., "A Case Report of Multiple Lumbar Spondylolyses With Spondylolisthesis," *Clinical Orthopaedic Surgery*, vol. 23, No. 3, pp. 311–314, 1988.

M. Maeshiro, K. Otani, K. Shibasaki, S. Nakai, K. Nemoto, M. Yoshida, "Posterior Fracture–Dislocation of the Thoracic Spine; Two Case Report," *Orthopedic Surgery*, vol. 39, No. 9, pp. 1373–1377, 1988–9.

Kunio Takaoka, "Clinical Application of Ceramic Implants in Orthopedics Surgery, *Medicina Philosophics*, vol. 4, No. 7, pp. 546–552, 1985.

Y. Yamano, Y. Mikawa, R. Watanabe, et al., "Anterior Body Fusion of Lumbar Degenerative Spondylolisthesis," *Journal of the Western Japanese Research Society For Spine*, vol. 13, pp. 46–50.

Dual Chisel and Its Bank Bones (Skimud Subkortikale Bones) For Posterior Lumbar Interbody Fusion –In Order To Simplify and Regularize the Surgical Procedure," *Orthopaedic Surgery*, vol. 11, pp. 150–3.

Vertebral Body Distraction System (Caspar), *"Orthopaedic Surgery"*, vol. 11, pp. 135–139.

Takayoshi Ueda, et al., "Instrumentation Surgery of Lumbar Interbody Fusion, *Central Japan Journal of Orthopaedic & Traumatic Surgery*, pp. 87–89.

Haruo Tsuji, et al., "Development and Clinical Application of Artificial Intervertebral Disc For Cervical Disc Lesions," *Central Japan Journal of Orthopaedic & Traumatic Surgery*, pp. 1505–1506.

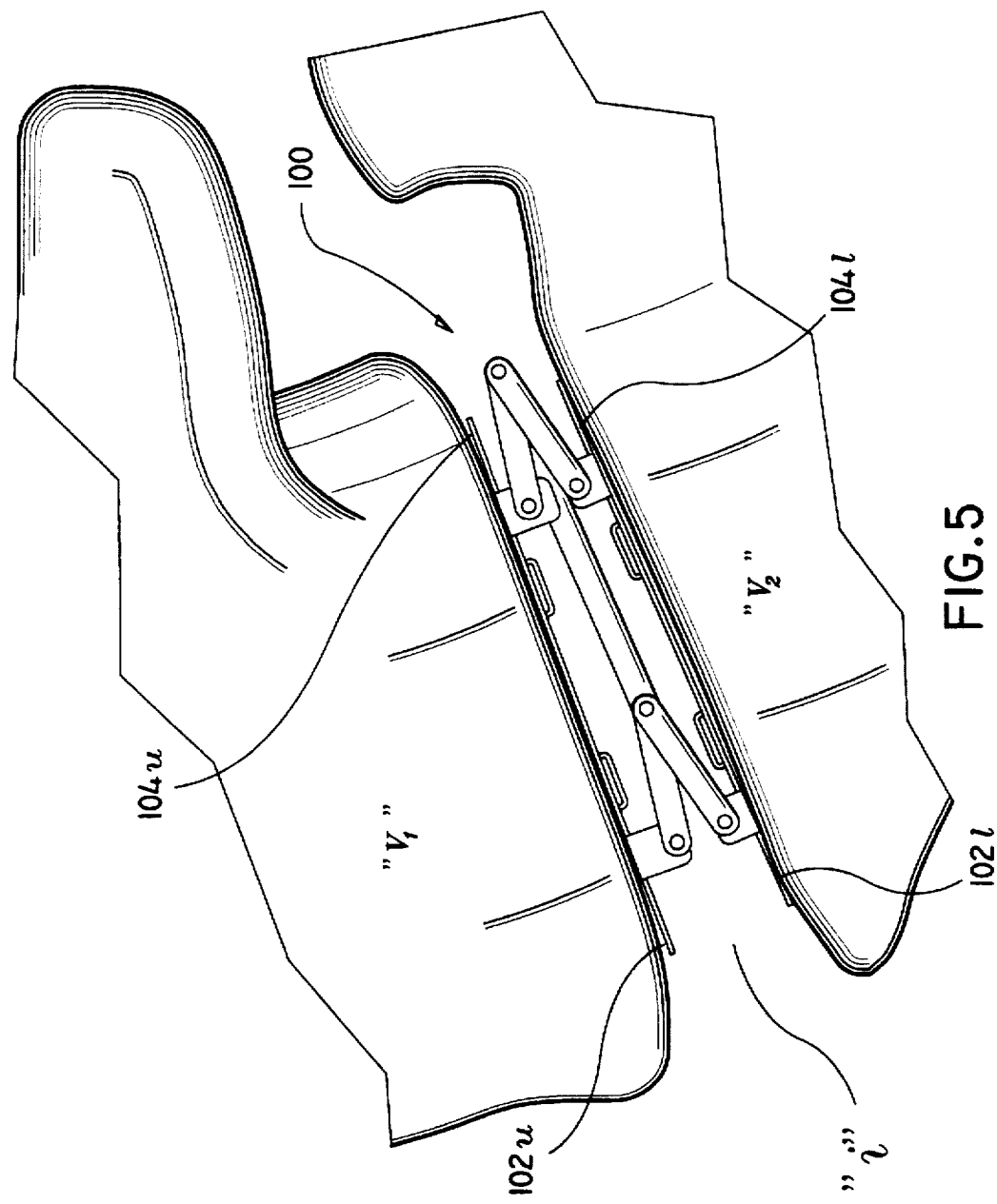
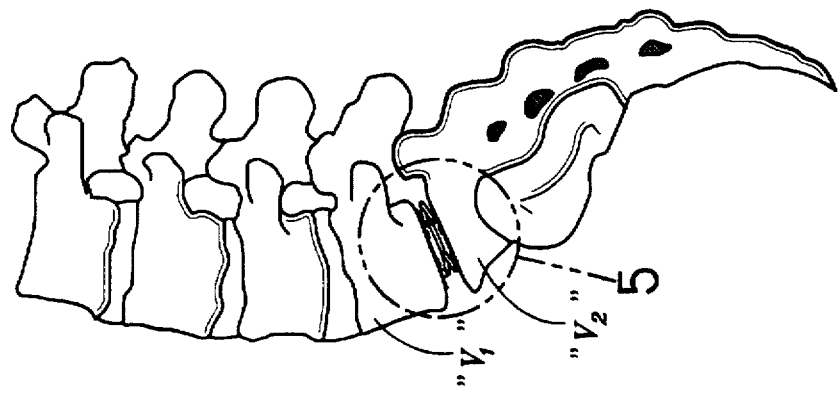

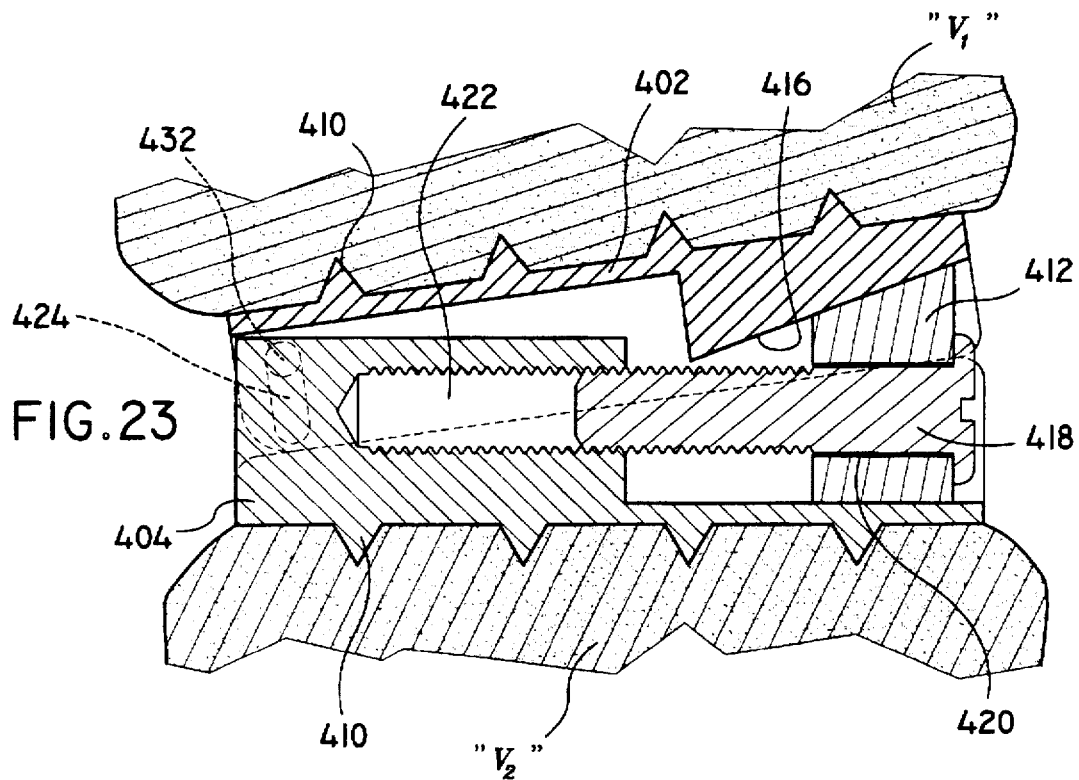
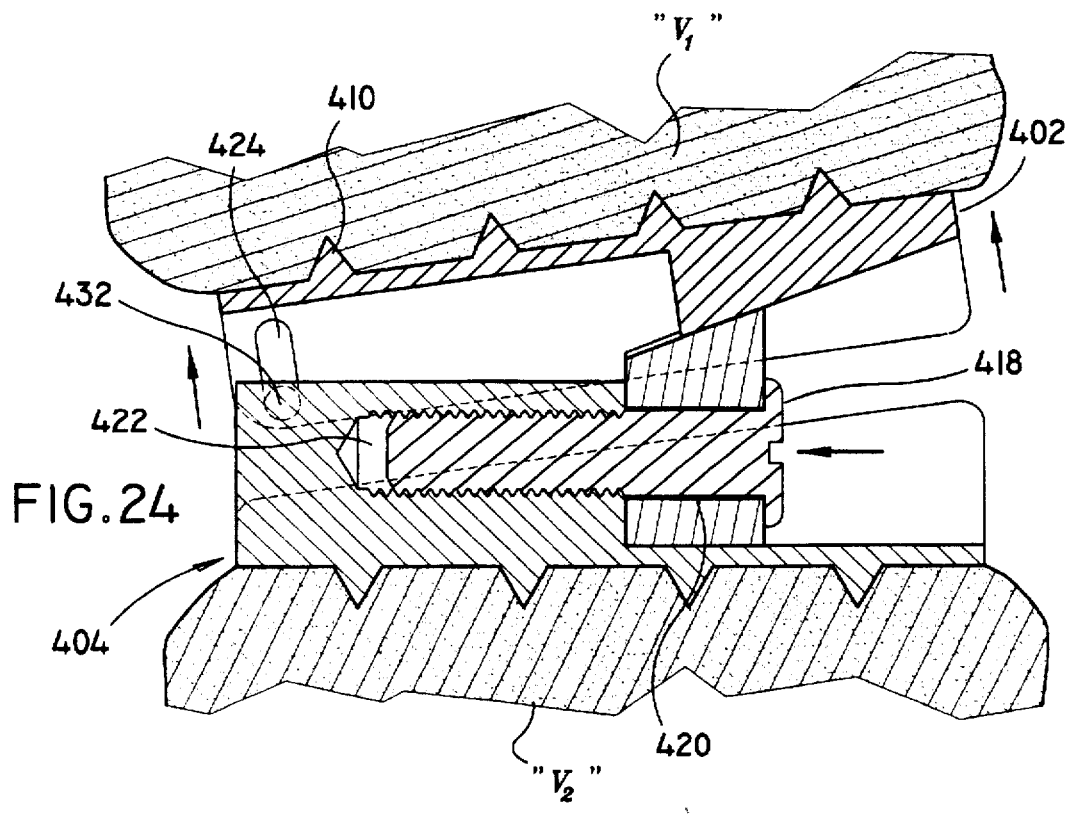

5,782,832

SPINAL FUSION IMPLANT AND METHOD OF INSERTION THEREOF

BACKGROUND

1. Technical Field

The present disclosure relates generally to a surgical apparatus for fusing adjacent bone structures, and, more particularly, to an apparatus and method for fusing adjacent vertebrae.

2. Background of the Related Art

The fusion of adjacent bone structures is commonly performed to provide for long-term replacement to compensate for degenerative or deteriorated disorders in bone. For example, an intervertebral disc which is a ligamentous cushion disposed between adjacent vertebrae, may undergo deterioration as a result of injury, disease, tumor or other disorders. The disc shrinks or flattens leading to mechanical instability and painful disc translocations.

Conventional procedures for disc surgery include partial or total excision of the injured disc portion, e.g., discectomy, and replacement of the excised disc with biologically acceptable plugs or bone wedges. The plugs are driven between adjacent vertebrae to maintain normal intervertebral spacing and to achieve, over a period of time, bony fusion with the plug and opposed vertebrae. For example, U.S. Pat. No. 4,887,020 to Vich discloses a cylindrical bone plug having a thread on its exterior, which is screwed into a correspondingly dimensioned cylindrical bore drilled in the intervertebral space.

Other devices and methods for intervertebral fusion are disclosed in U.S. Pat. Nos. 4,863,477 to Monson; 4,874,389 to Downey; 4,932,969 to Fray et al; 5,306,307 to Senter et al; 5,306,308 to Gross et al.; and 5,401,269 to Buttner-Janz et al. The Monson '477 device discloses a synthetic intervertebral disc prosthesis molded in the same shape and general dimensions as a natural disc. The prosthesis includes two halves joined together to form a body having a fluid-tight cavity in its interior. The upper and lower surfaces of the disc each have a plurality of small suction cup-like projections molded thereon for frictionally engaging the adjacent vertebrae. The prosthesis is inserted within the intervertebral space and a volume of fluid is injected into the interior cavity of the prosthesis to create the necessary amount of resiliency which restores proper vertebral spacing.

More recently, emphasis has been placed on fusing bone structures (i.e., adjoining vertebrae) with prosthetic cage implants. One fusion cage implant is disclosed in commonly assigned U.S. Pat. No. 5,026,373 to Ray et al. The Ray '373 fusion cage includes a cylindrical cage body having a thread formed as part of its external surface and apertures extending through its wall which communicate with an internal cavity of the cage body. The fusion cage is inserted within a tapped bore or channel formed in the intervertebral space. The adjacent vertebral bone structures communicate through the apertures with bone growth inducing substances within the internal cavity to unite and eventually form a solid fusion of the adjacent vertebrae.

SUMMARY

Accordingly, the present disclosure is directed to further improvements in the fusion of adjacent bone structures, e.g., adjacent vertebrae. In a preferred embodiment, an implant for insertion within an intervertebral space between adjacent vertebrae for supporting the vertebrae in predetermined spaced relation is disclosed. The implant includes lower and upper plate members dimensioned for at least partial insertion within the intervertebral space and having contacting surfaces for engaging respective vertebral end faces of the adjacent vertebrae. A linkage mechanism including at least one link member operatively connects the lower and upper plate members. The linkage mechanism is actuable to cause relative movement of the lower and upper plate members, wherein upon actuation, the contacting surfaces of the lower and upper plate members engage the vertebral end faces with the lower and upper plate members supporting the adjacent vertebrae in spaced relation during healing. The linkage mechanism is preferably adapted to cause lateral displacing movement of at least one plate member upon actuation thereof such that contacting surfaces of the lower and upper plate members are in general parallel relation when in the deployed position. Preferably, the contacting surfaces of the lower and upper plate members have discontinuities to engage the vertebral end plates. The discontinuities may be in the form of projections dimensioned for penetrating the vertebral end plates. The lower and upper plate members may further include at least one opening extending therethrough to permit bone ingrowth.

In another preferred embodiment, an implant for insertion within the intervertebral space includes first and second plate members having engaging surfaces with discontinuities to engage vertebral end faces of the vertebrae, and at least one resilient member disposed between the first and second plate members to bias the first and second plate members to a generally open spaced arrangement. The one resilient member is configured and dimensioned to exert forces on the plate members sufficient to support the adjacent vertebrae in spaced relation during healing while permitting relative movement thereof to accommodate variations in loads realized during normal flexural movement of the vertebral column. Preferably, the one resilient member is a coil spring member. A plurality of coiled spring members may be incorporated as well.

In another preferred embodiment, an implant for insertion within the intervertebral space includes at least first and second supporting members dimensioned for insertion within the intervertebral space and having contacting surfaces for contacting vertebral end faces of the adjacent vertebrae. The first member has an inner arcuate articulating surface cooperating with a correspondingly dimensioned outer arcuate articulating surface of the second member to permit articulating movement of the first member so as to accommodate movement of the vertebral column during healing. Articulating surfaces of the first and second plate members each define a constant radius of curvature with the radius of curvature of each of the first and second plate members being substantially equal.

The contacting surfaces of the first and second plate members each include a plurality of apertures to permit bone ingrowth. A resilient member may be disposed between the first and second support members to facilitate the absorption of compressive forces.

In yet another preferred embodiment, the implant includes at least first and second support members having engaging surfaces for engaging vertebral end plates of the vertebrae, and a camming arrangement having at least one camming member operatively engageable with the first and second support members. The camming member is moveable to move the first and second support members between a non-deployed position and a deployed position. The camming member includes a camming block having a camming surface which is engageable with a corresponding camming surface of at least one of the support members whereby, upon movement of the camming member, the camming surfaces interact to move the first and second support members between the non-deployed and the deployed positions. An actuating screw transverses a bore defined in the camming block and threadably engages a threaded bore associated with one of the first and second support members. The actuating screw is rotatable to cause corresponding movement of the camming block.

BRIEF DESCRIPTION OF THE DRAWINGS

Preferred embodiments of the disclosure are described hereinbelow with reference to the drawings wherein:

FIG. 4 is a view illustrating the implant in the collapsed position and inserted within an intervertebral space defined between adjacent vertebrae;

FIG. 5 is an isolated view further depicting the implant positioned within the intervertebral space;

FIG. 23 is a sectional view illustrating the implant in the retracted position positioned within the intervertebral space;

FIG. 24 is a view similar to the view of FIG. 23 illustrating the implant in the extended position;

DETAILED DESCRIPTION OF THE PREFERRED EMBODIMENT(S)

The apparatus of the present disclosure is intended for fusing adjacent bone structures and has particular application in the spinal fusion of adjacent vertebrae subsequent to a discectomy procedure. The apparatus may be implanted using any conventional surgical approach, e.g., anterior and/or posterior approaches, or may be implanted utilizing minimally invasive or endoscopic surgical techniques currently being utilized to carry out discectomy and spinal implant procedures.

Figure 1:
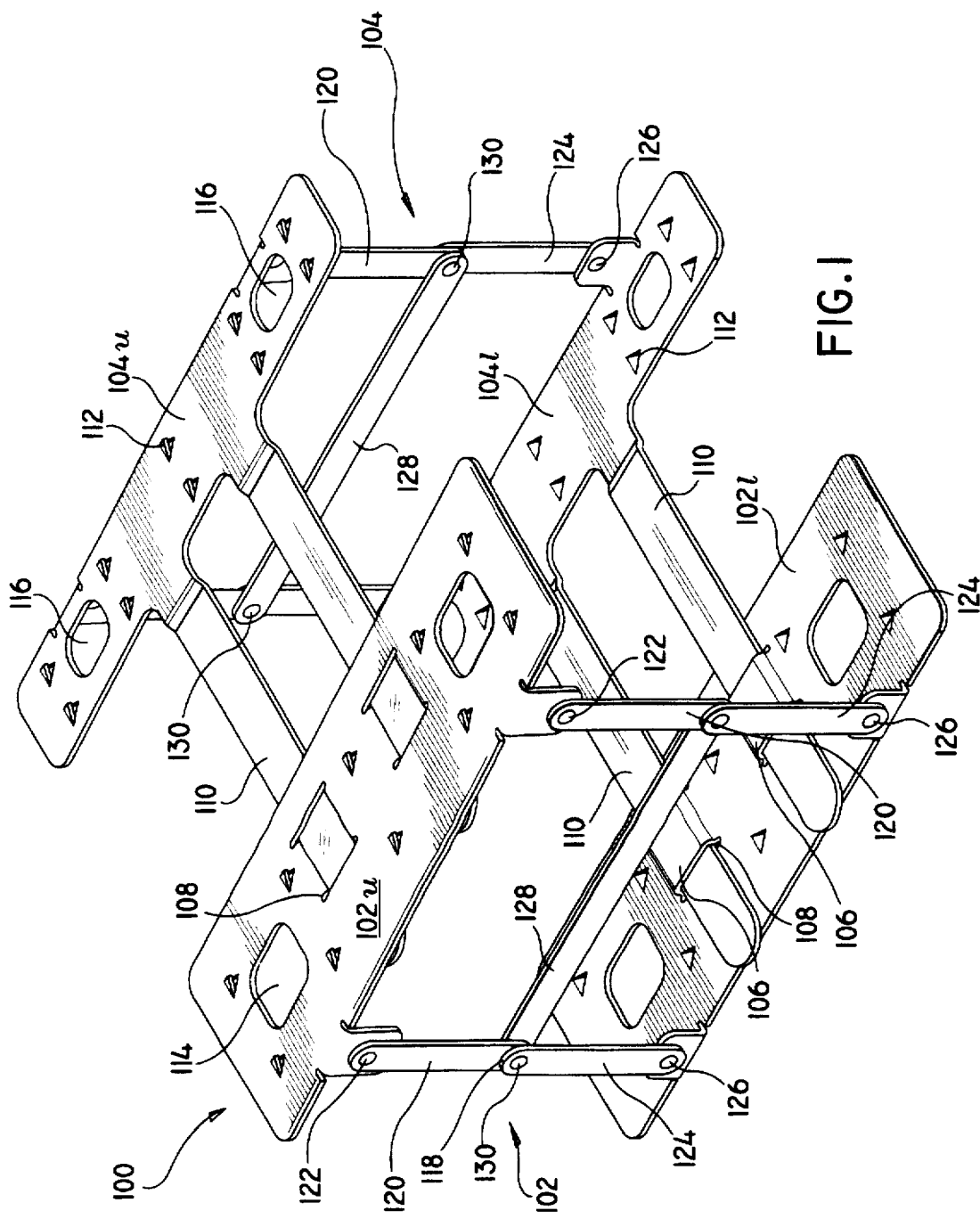
FIG. 1 is a perspective view of a preferred embodiment of the implant for facilitating spinal fusion constructed in accordance with the principles of the present disclosure.
Figure 2:
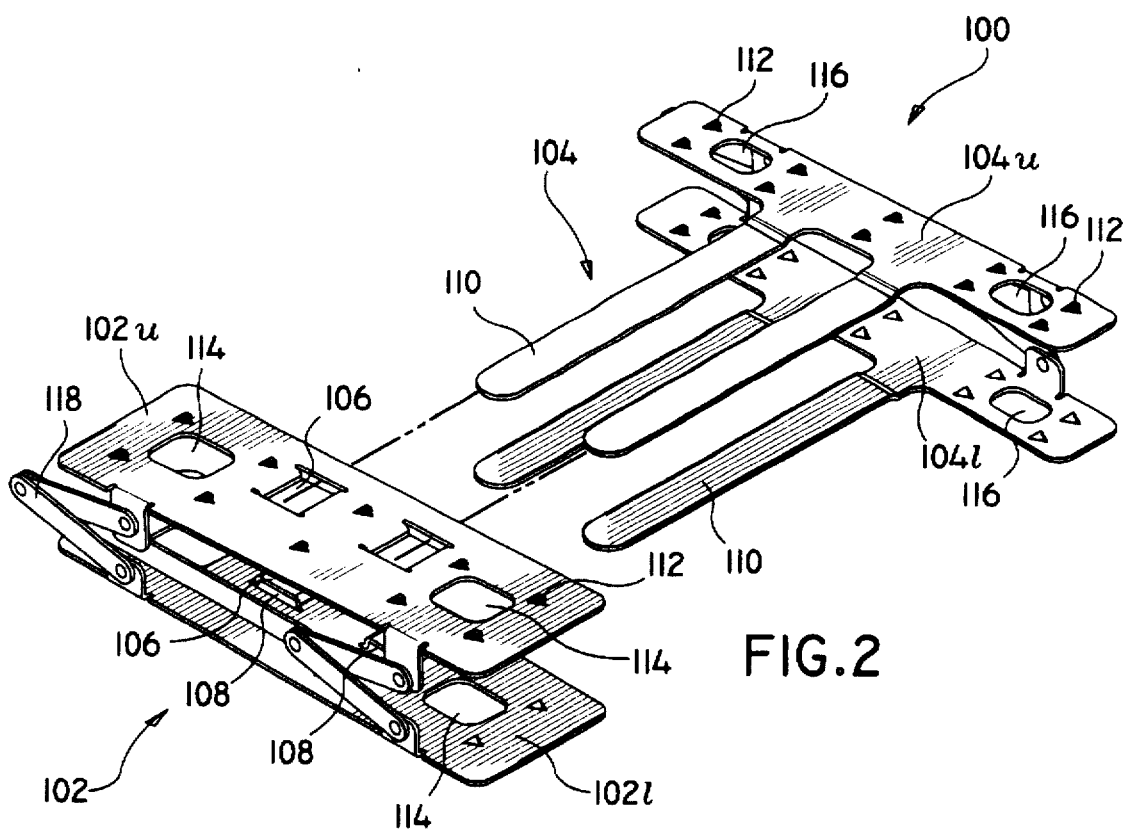
FIG. 2 is a perspective view with parts separated of the implant of FIG. 1.
Figure 3:
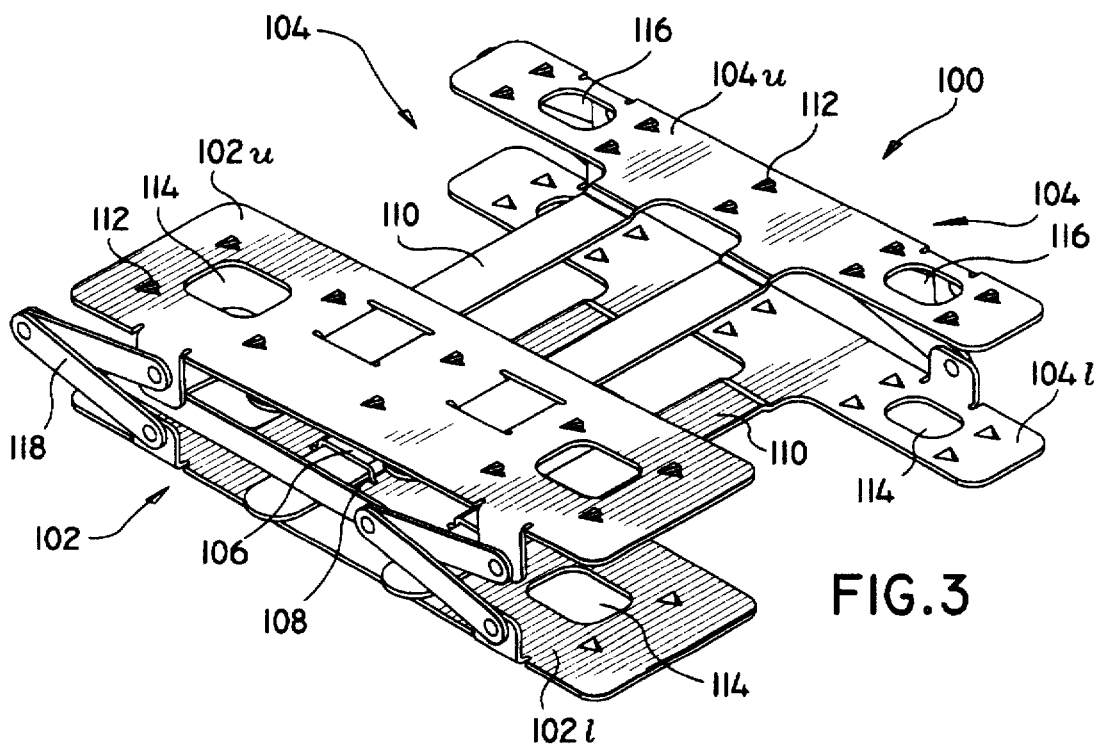
FIG. 3 is a perspective view of the implant in a collapsed position.

Referring now to FIGS. 1–3, there is illustrated the apparatus constructed in accordance with the principles of the present disclosure. Apparatus 100 includes two separable support components 102, 104 which are adapted for adjusting sliding movement relative to each other to selectively vary the overall width of the implant. Support component 102 has upper and lower support plates 102$u$, 102$l$ while support component 104 has upper and lower plates 104$u$, 104$l$. As shown, plates 102$u$, 102$l$ of component 102 each have a greater width than plates 104$u$, 104$l$ of component 104.

Upper and lower plate portions 102$u$, 102$l$ of support component 102 each include two raised portions 106 extending generally transversely therefrom which define longitudinal slots 108. Upper and lower plates 104$u$, 104$l$ each have two transverse tongue portions 110 extending therefrom which are correspondingly dimensioned to be received within transverse slots 108 to mount support component 104 to support component 102. Tongue portions 110 are strategically dimensioned to slide within slots 108 thereby permitting selective adjusting movement of the component 104 relative to component 102. In this manner, the overall width of implant 100 may be varied to accommodate vertebral columns of various sizes or to increase or minimize the supporting capacity of the implant during healing. In particular, support components 102, 104 may be selectively moved toward each other via the tongue and slot arrangement to decrease the overall width of the implant 100 thereby permitting more lateral movement of the vertebral column during healing. On the other hand, support components 102, 104 may be moved away from each other to increase the overall width of the implant thereby providing a more stabilizing effect to the vertebral column.

Referring still to FIGS. 1–3, upper plate portions 102$u$, 104$u$ and lower plate portions 102$l$, 104$l$ each possess associated outer contacting surfaces which engage the vertebral end faces. The contacting surfaces define discontinuities to assist in engaging the vertebral end faces upon insertion within the intervertebral space. Preferably, the discontinuities are in the form of triangular-shaped projections 112 extending from the contacting surfaces, which define pointed edges to penetrate the vertebral end faces to thereby resist tendency of the implant to move or become dislodged once positioned within the adjacent bone structures. Other discontinuities are envisioned as well such as knurling, bristle-coatings, etc . . . Upper plate portions 102u, 104u and lower plate portions 102l, 104l also include apertures 114, 116. Apertures 114, 116 permit bone ingrowth through their respective plates to facilitate fusion of the implant with the vertebral bodies.

As best depicted in FIG. 1, linkage mechanism, identified generally by reference numeral 118, respectively operatively connects upper and lower plate portions 102 u, 102l and upper and lower plate portions 104u, 104l. Each linkage mechanism 118 is preferably identical and includes transverse connecting links 120 connected to opposed ends of upper plate portions 102u, 104u through pins 122 and transverse connecting links 124 connected to opposed ends of lower plate portions 102l, 104l through pins 126. Connecting links 120, 124 are interconnected by longitudinal links 128 through pins 130. Each linkage mechanism 118 is moveable between the extended position shown in FIG. 1 where upper and lower plate portions are at their most displaced position and a collapsed position shown in FIG. 3.

Referring now to FIGS. 4–5, the implant 100 is shown positioned within the intervertebral space "i" defined between adjacent vertebrae "$V_1$, $V_2$". Implant 100 is typically inserted within the intervertebral space "i" subsequent to a discectomy procedure. Discectomy involves removal of a least a portion of the degenerated disc material with the use of the cutting instruments (not shown) e.g., scalpels, rongeurs, etc...

Figure 6:
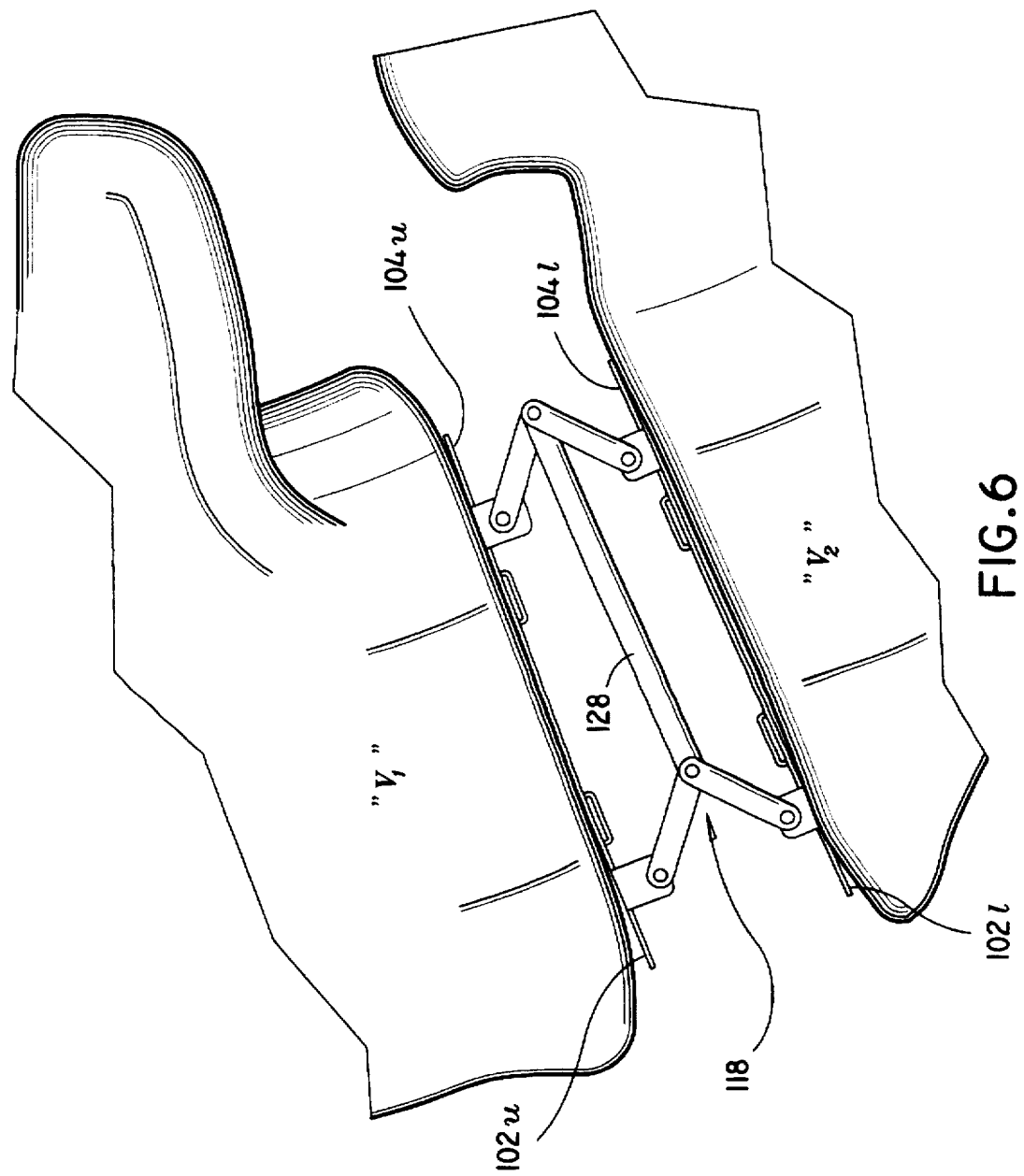
FIG. 6 is a view similar to the view of FIG. 5 illustrating the implant in its extended position supporting the adjacent vertebrae in spaced relation.

Prior to insertion, the width of implant 100 is adjusted by selectively adjusting the relative positioning of support components 102, 104 through the tongue and slot arrangement in the manner discussed above. Implant 100, in its collapsed condition, is thereafter positioned within the intervertebral space "i" with the use of a grasping instrument (not shown). As mentioned, conventional anterior or posterior approaches, as well as laparosopic approaches, may be utilized. In the collapsed condition, implant 100 presents a reduced profile which facilitates its insertion. Once implant 100 is inserted and appropriately positioned, the linkage mechanisms 118 are actuated to displace upper plate portions 102u, 104u from lower plate portions 102l, 104l to move the implant to at least a partially extended position shown in FIG. 6. In this position, upper and lower plate portions 102u, 104u, 102l, 104l contact the vertebral end plates of the adjacent vertebrae in supporting engaged relation with triangular projections 112 of the plate portions penetrating the end plates to securely fix the implant member within the intervertebral space. In the deployed or extended position of FIG. 6, implant 100 forms a strut between adjacent vertebrae "$V_1$ $V_2$" supporting the vertebrae in desired spaced relation. Linkage mechanisms 118 sufficiently support components 102,104 in the extended position. It is envisioned that linkage mechanisms 118 may be locked in the deployed position by conventional arrangements such as with locking screws, etc . . . As shown, upper plate portions 102u, 104u are in general parallel relation with lower plate portions 102l, 104l. Over a period of time, the adjacent vertebral tissue communicates through apertures 114, 118 defined in the support components 102, 104 to form a solid fusion.

It is envisioned that the interior cavity of implant 100 defined between the upper and lower plate portions may be packed with bone growth inducing substances as known in the art prior to insertion to facilitate the fusion process.

Figure 7:
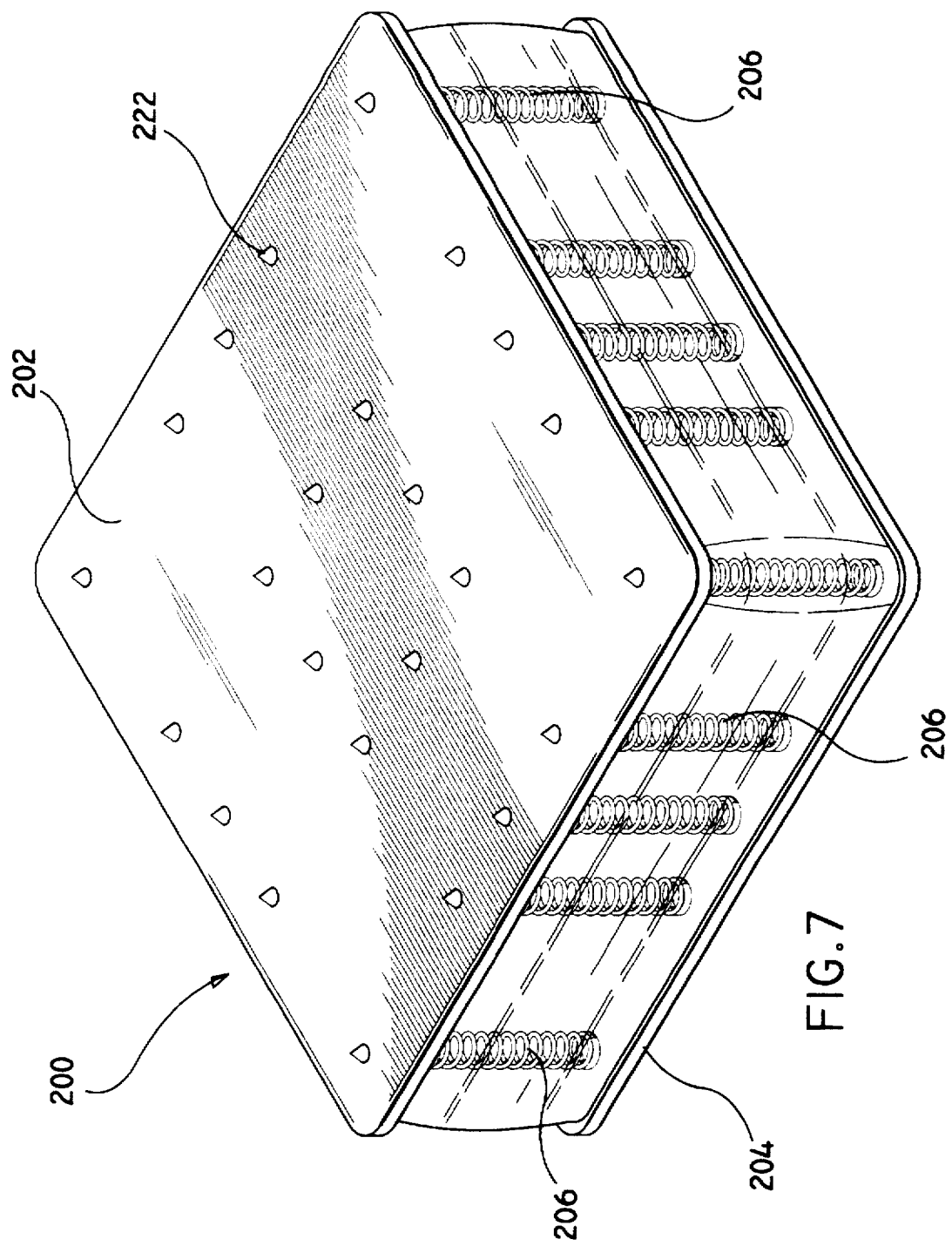
FIG. 7 is a perspective view of an alternate embodiment of the implant of FIG. 1.
Figure 8:
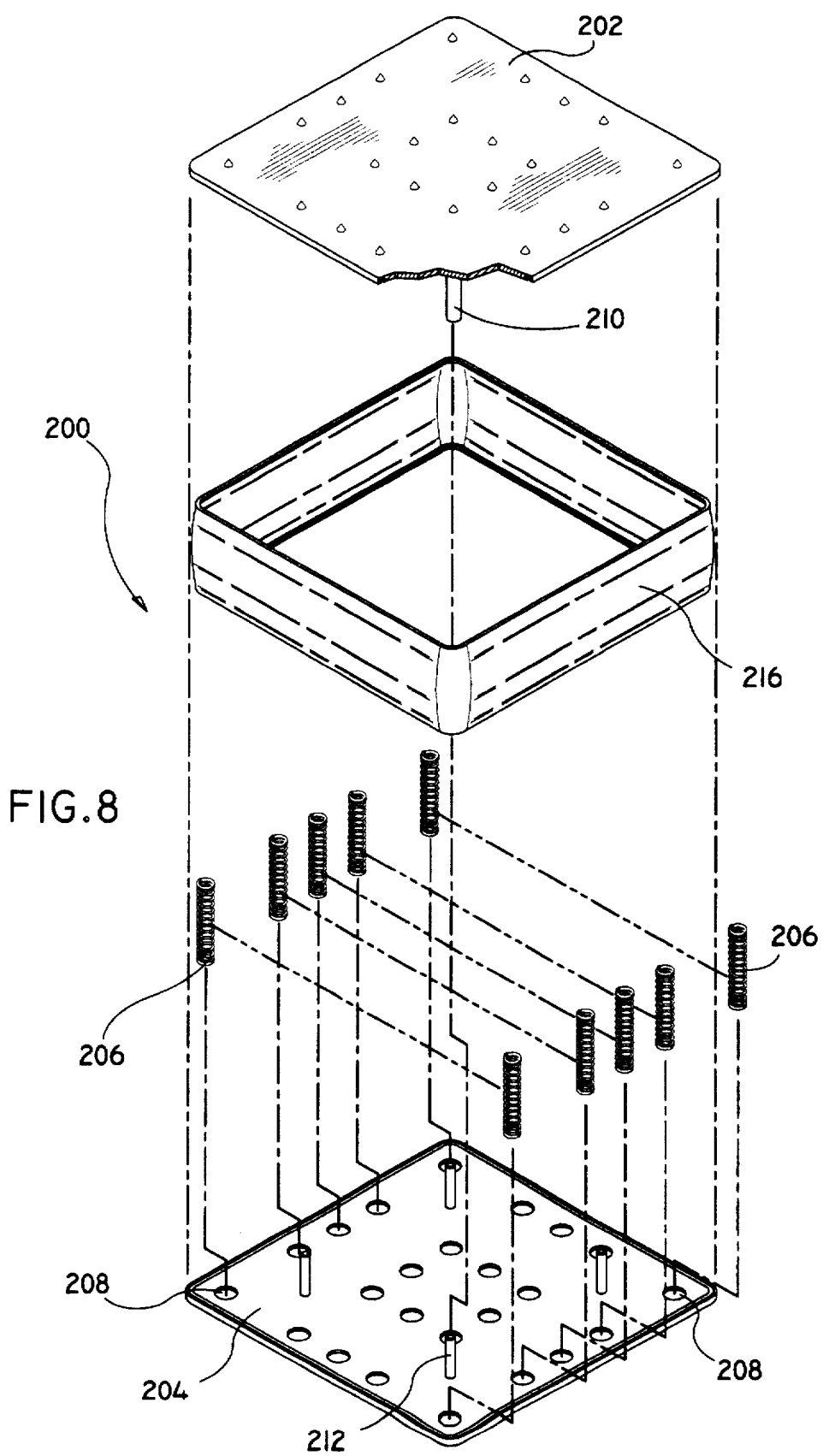
FIG. 8 is a perspective view with parts separated of the implant of FIG. 7 illustrating the first and second support members, support springs disposed between the support members and a flexible cover surrounding the support spring.

Referring now to FIGS. 7–8, there is illustrated an alternate embodiment of the spinal implant of the present disclosure. Implant 200 is intended to be used in a similar manner to that described in connection with implant 100 of FIG. 1, i.e., within the intervertebral space defined between adjacent vertebrae subsequent to a discectomy procedure. Implant 200 includes first and second plate members 202, 204 supported in spaced relation by a plurality of coiled support springs 206 which are disposed between the plate members 202, 204. Springs 206 are received in correspondingly dimensioned impressions 208 defined in the inner surfaces of first and second plate members 202, 204 and extend in a generally transverse direction relative to each plate 202, 204 as shown. Support springs 206 permit deflecting movement, e.g., compressive movement of first and second plate members 202, 204 to permit flexural compressive movement of the vertebral column. Springs 206 are correspondingly dimensioned to provide sufficient force to withstand extreme compressive forces exerted by the spinal column.

Figure 9:
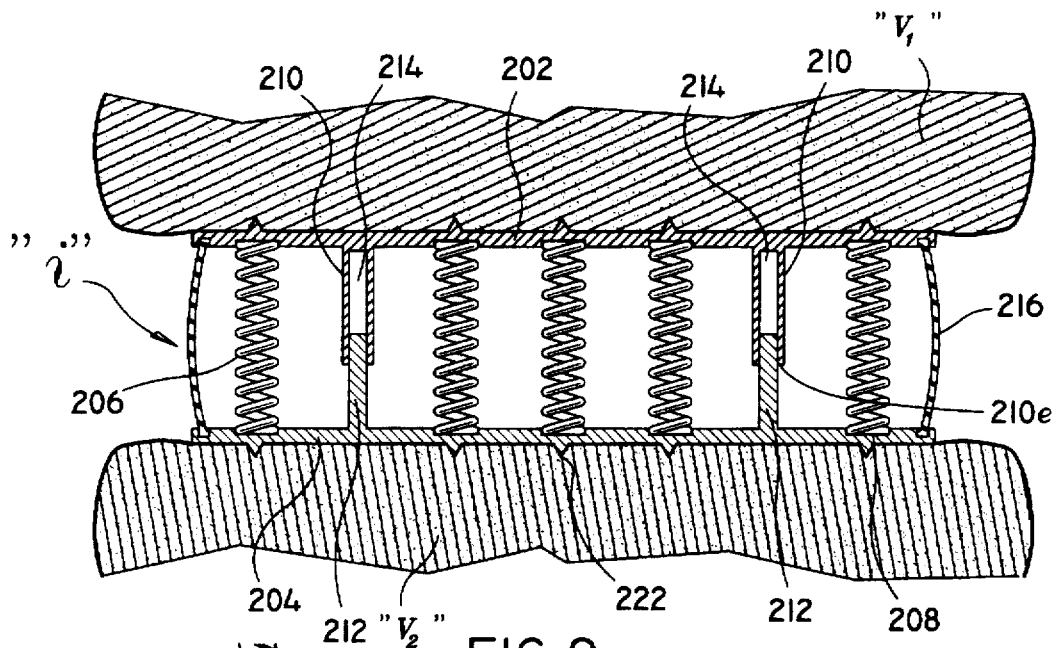
FIG. 9 is a sectional view illustrating the implant positioned within the intervertebral space.

As best depicted in FIGS. 8–9, first plate 202 includes a plurality (e.g., four) of transversely extending rigid tubular portions 210. Second plate 204 includes a plurality (e.g., four) of transversely extending rigid rod portions 212 extending from the inner surface thereof. Rod portions 212 are correspondingly dimensioned to be received within inner bores 214 defined by the tubular portions 210 to facilitate mounting of the first and second plate members 202, 204. In particular, the tubular portion 210 and rod portion 212 arrangement functions in preventing lateral movement of the first plate member 202 relative to the second plate member 204. The arrangement also serves in limiting the amount of compressive movement of plate members 202, 204 by engagement of the remote ends 210e of the tubular portions 210 with the inner surface of plate member 204. It is to be noted that tubular portions 210 are appropriately dimensioned to permit reciprocating movement of the rod portions 212 therein during compressive movement of the vertebral column.

Figure 10:
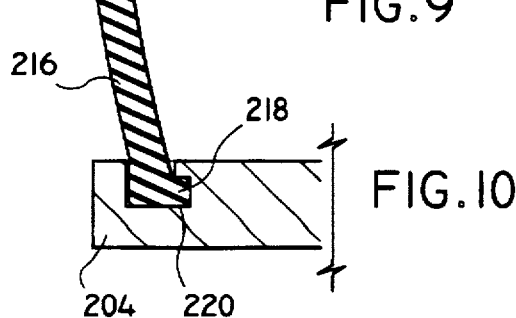
FIG. 10 is an isolated view illustrating a preferred arrangement for mounting the flexible cover about the support members.

Referring to FIGS. 9–10, in conjunction with FIG. 8, a flexible cover 216 may be positioned about the periphery of implant 100 to enclose the coiled spring members 206. Cover 216 is preferably fabricated from a suitable biocompatible material. Cover 216 functions in preventing bone ingrowth from contacting the coiled support springs 206. Bone ingrowth within support spring 206 may potentially degrade the functioning of springs 206. Cover 216 is preferably mounted to upper and lower plate members 202, 204 through a tongue and groove arrangement shown in detail in FIG. 10. Preferably, the outer ends of flexible cover 216 define a tongue 218 which is accommodated within corresponding recesses 220 formed in first and second plate members 202, 204.

Figure 11:
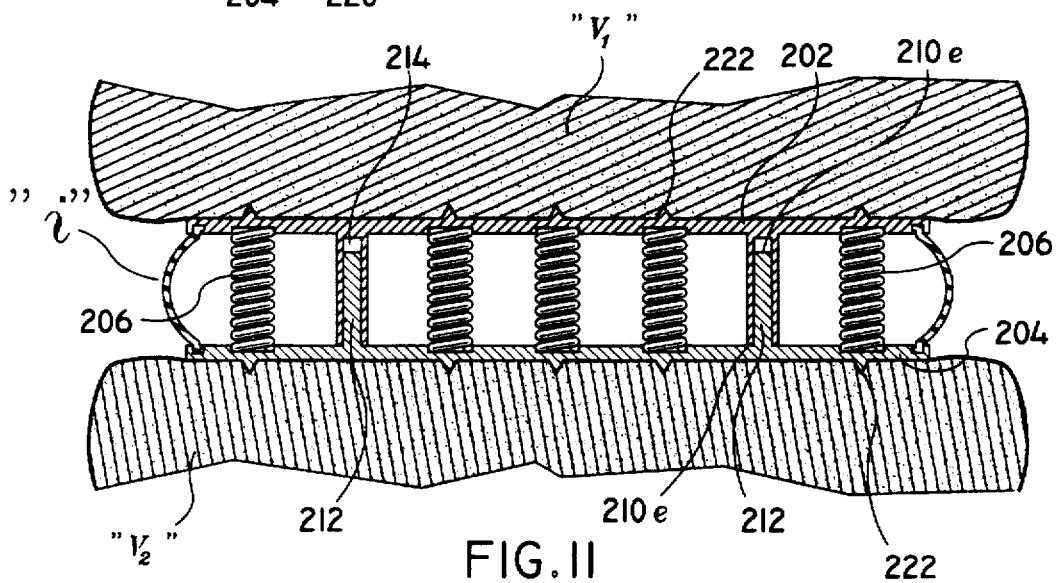
FIG. 11 is a view similar to the view of FIG. 9 illustrating the implant slightly compressed during normal flexural movement of the vertebral column.
Figure 12:
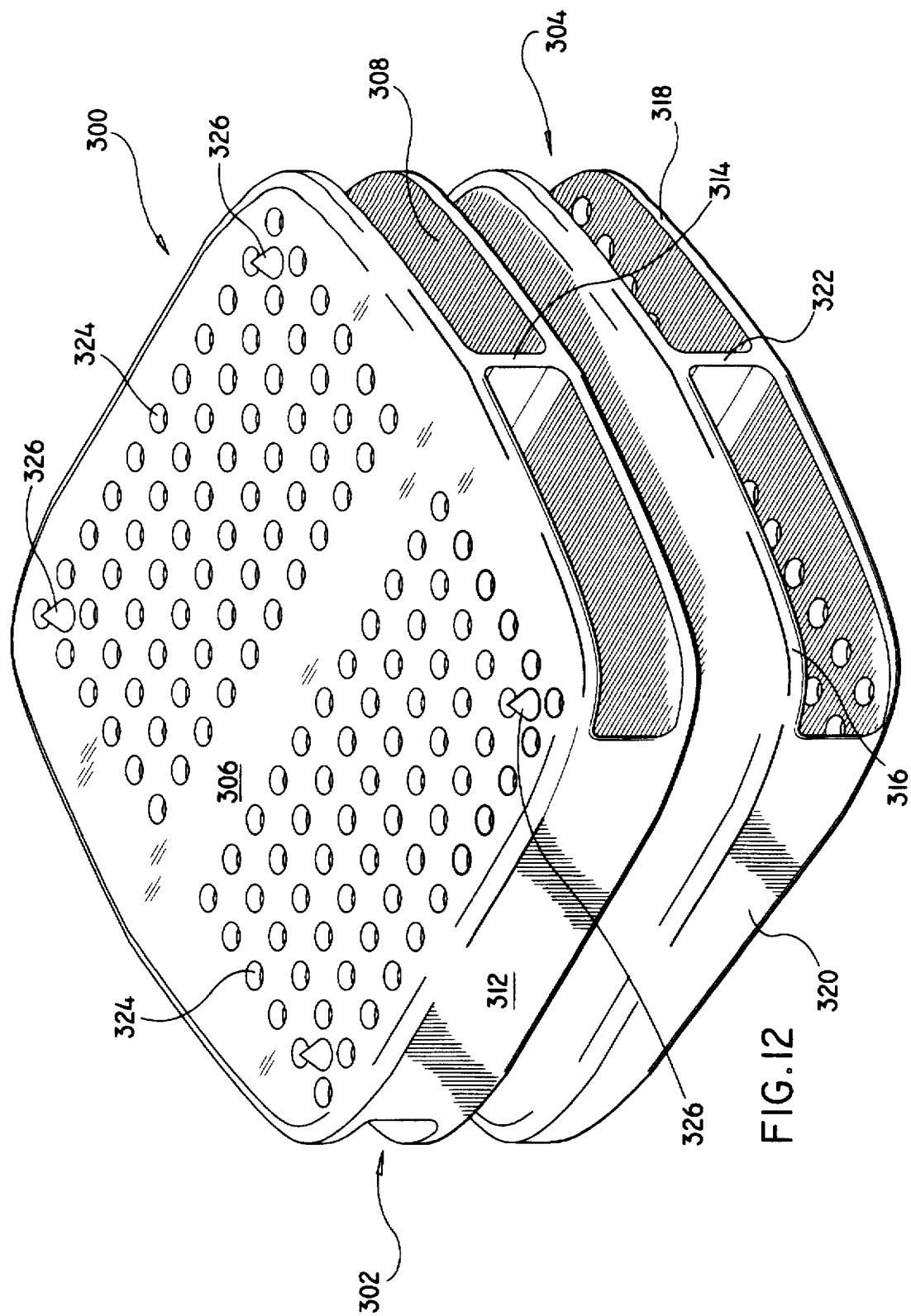
FIG. 12 is a perspective view of another alternate embodiment of the spinal implant.

FIGS. 9 and 11 depict implant 100 positioned within the intervertebral space "i" defined between adjacent vertebrae "$V_1V_2$". FIG. 9 illustrates implant 100 in a fully extended position corresponding to a minimal load exerted on the vertebral column. FIG. 11 illustrates implant 100 in a compressed condition when the vertebral column is subjected to a large compressive load with support springs 206 absorbing the load. In addition, in the inserted position of implant 200, pyramid-shaped projections 222 extending from the contacting surface 202, 204 penetrate the vertebral end plates of the "$V_1$, $V_2$" to facilitate mounting of the implant 200 within the intervertebral space "i", and to prevent the implant 200 from becoming dislodged prior to achieving full fusion with the adjacent vertebrae "$V_1$, $V_2$".

Referring now to FIGS. 12–17 there is illustrated another alternate embodiment of the spinal implant of the present disclosure. Spinal implant 300 includes first and second support members 302, 304 which supportingly engage adjacent vertebrae "$V_1$, $V_2$" upon insertion within an intervertebral space "i". Support member 302 includes a pair of parallel plates 306, 308 interconnected to each other through transverse side plate portions 312 and transverse intermediate plate portion 314. Similarly, second support member 304 includes a pair of parallel plate portions 316, 318 interconnected by side plate portions 320 and intermediate plate portion 322. First support member 302 and second support member 304 are preferably each integrally formed to form a single unit and may be fabricated from a ceramic material, a biocompatible metallic material or a biocompatible polymeric material. The respective upper and lower plate portions 306, 318 of first and second support members 302, 304 have tissue contacting surfaces which define discontinuous surfaces to permit bone ingrowth during fusion. In a preferred embodiment, the discontinuous surfaces include a plurality of apertures 324 which permit bone ingrowth and a plurality of projections 326 which are disposed on a peripheral area of the respective plate portions. Projections 326 define penetrating tip portions which engage the vertebral end plate upon application within the intervertebral space.

Figure 13:
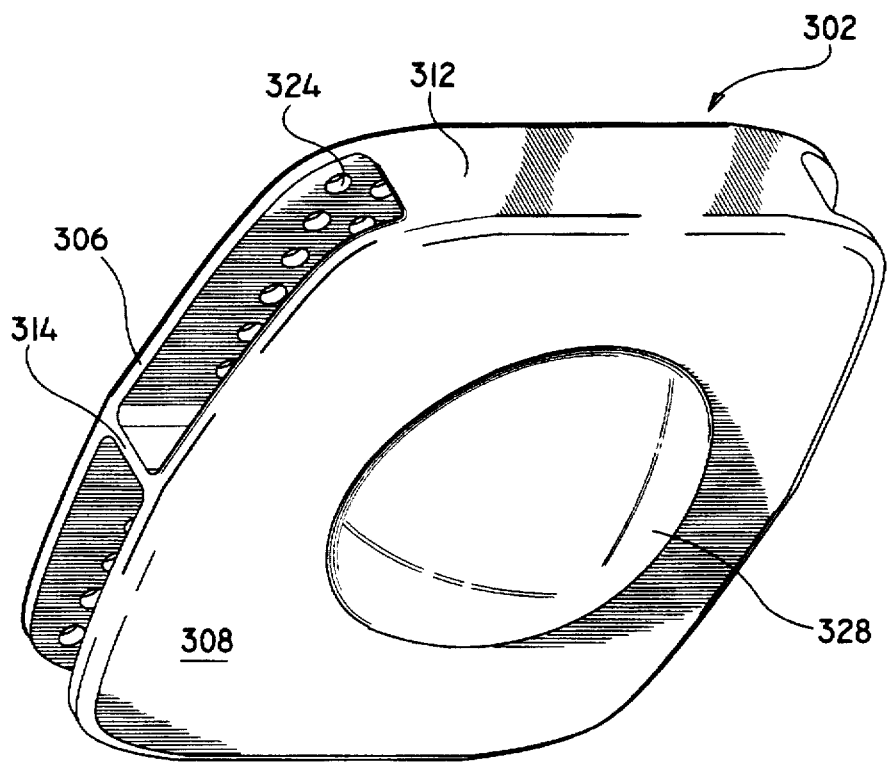
FIGS. 13–14 are perspective view of the respective upper and lower support members of the implant of FIG. 12 illustrating the ball and socket arrangement for permitting relative articulating movement of the support members.
Figure 14:
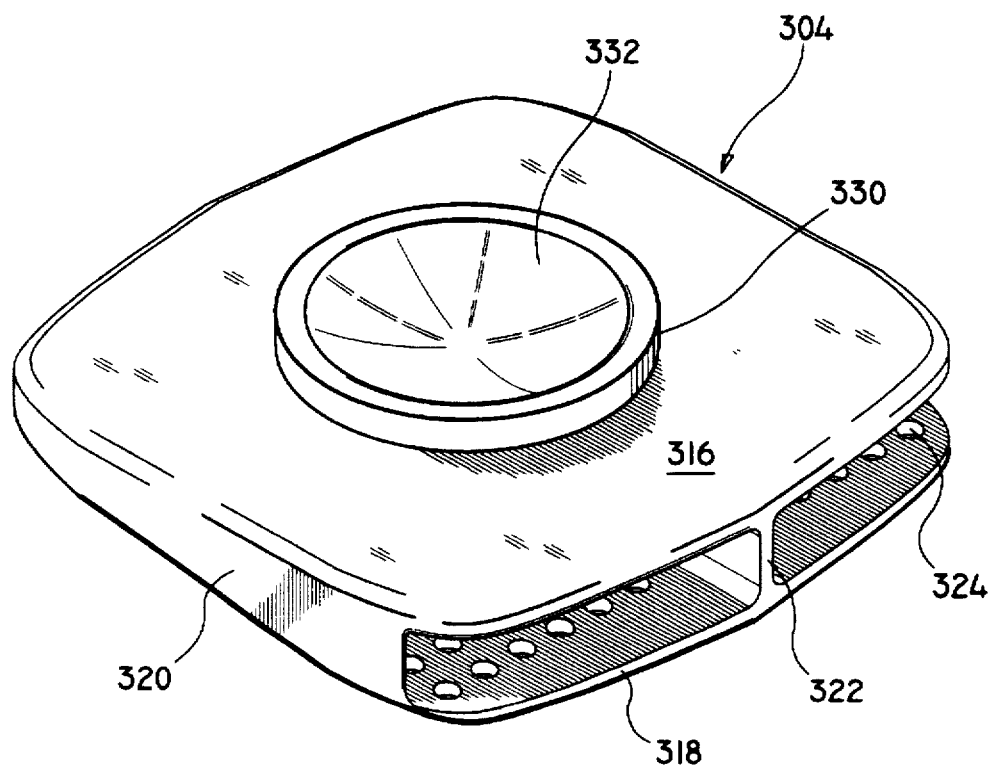
Figure 15:
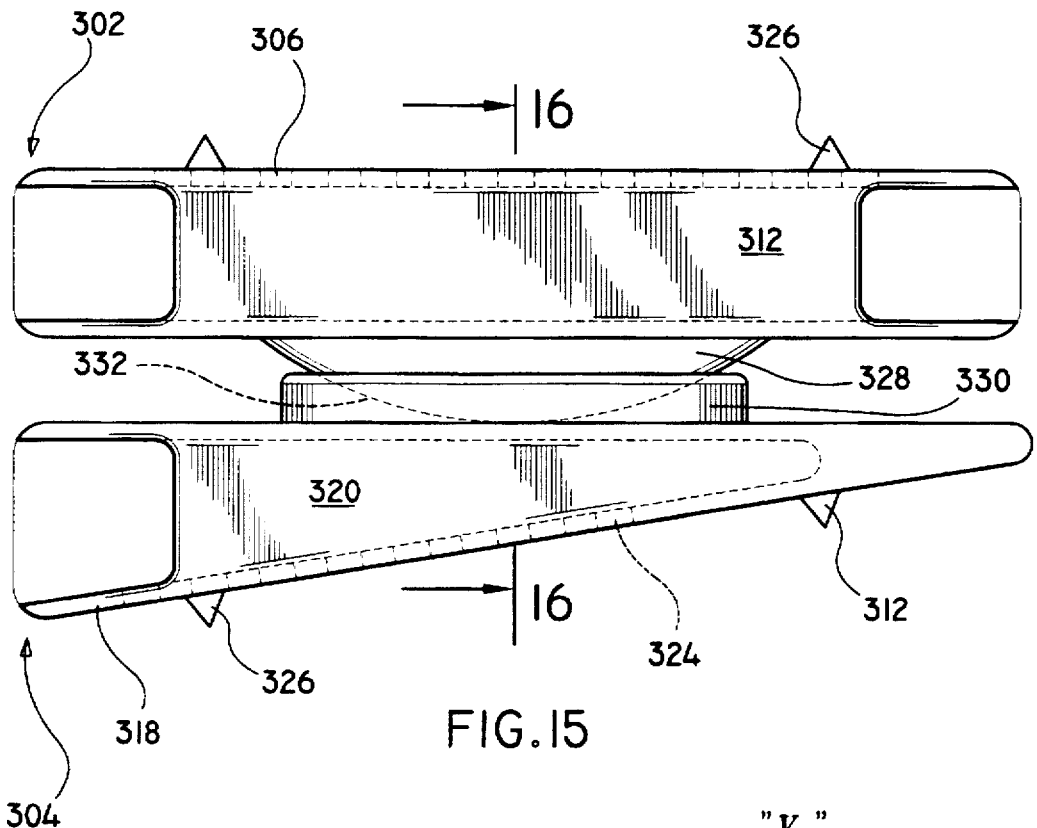
FIG. 15 is a side plan view of the spinal implant of FIG. 12 in the assembled condition.

Referring now to FIGS. 13–15, first and second support members 302, 304 are supported in general spaced relation by a ball and socket arrangement. In particular, first support member 302 has an integrally formed spherical portion 328 extending from lower plate 308. Second support member 304 has a projecting portion 330 extending from upper plate 316 and defining a generally spherical recess or socket 332 correspondingly dimensioned to accommodate spherical portion 328 of first support member 302. Spherical portion 328 is capable of articulating movement within socket 332 thereby permitting the vertebral column to flex through a generally "normal" range of motion. Preferably, spherical portion 328 and socket 332 define generally equivalent radii of curvatures.

Figure 16:
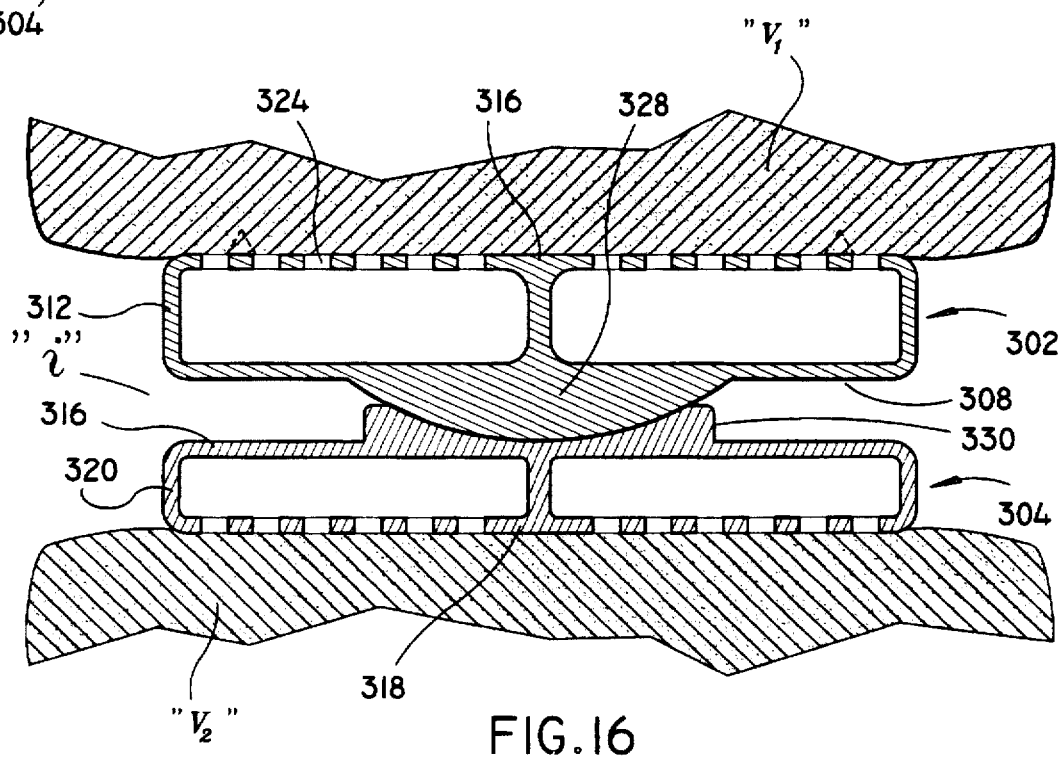
FIG. 16 is a sectional view illustrating the implant positioned within the intervertebral space.
Figure 17:
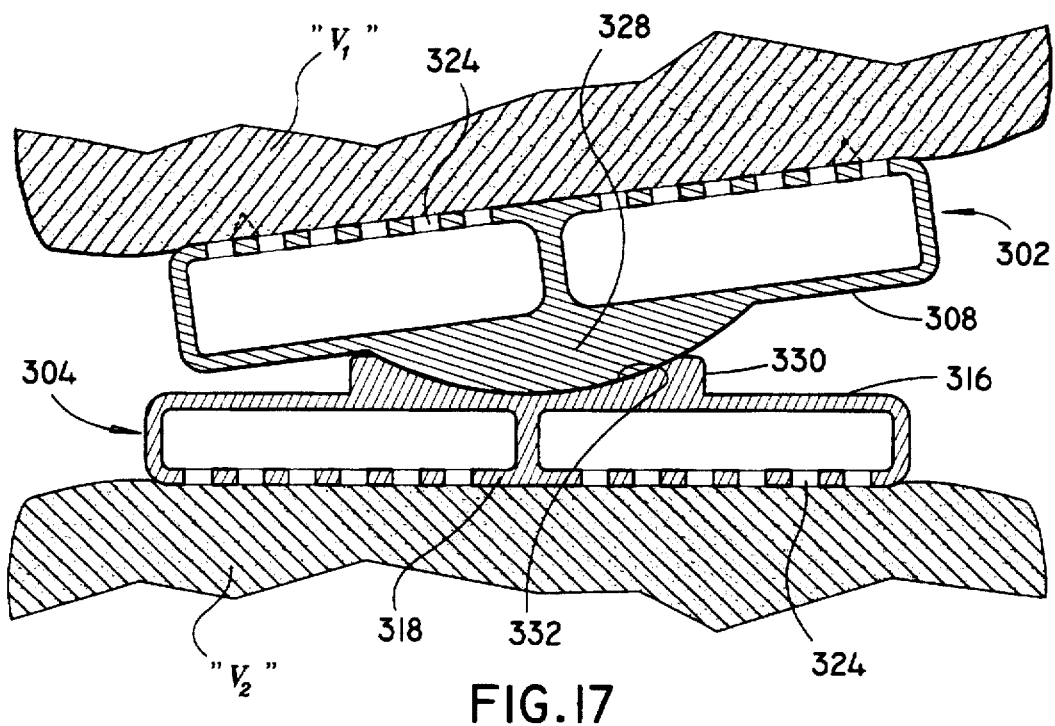
FIG. 17 is a view similar to the view of FIG. 16 illustrating articulating movement of the upper support member via the ball and socket arrangement.

FIGS. 16 and 17 depict spinal implant 300 disposed within the intervertebral space "i" defined between adjacent vertebrae "$V_1$, $V_2$". As shown in FIG. 16, implant 300 supportingly contacts the upper and lower vertebrae "$V_1$, $V_2$" through the engagement of first support member 302 and second support member 304 with the vertebral end faces. Projections 326 extending from the upper and lower plate portions 316, 318 of first and second support members 302, 304 penetrate the vertebral end faces to assist in retaining the implant 300 within the intervertebral space "i" during healing.

FIG. 17 illustrates the articulating movement of the first support member 302 relative to the second support member 304 during movement of the spine. As shown, spherical portion 328 slides within socket 332 to permit such articulating movement.

Figure 18:
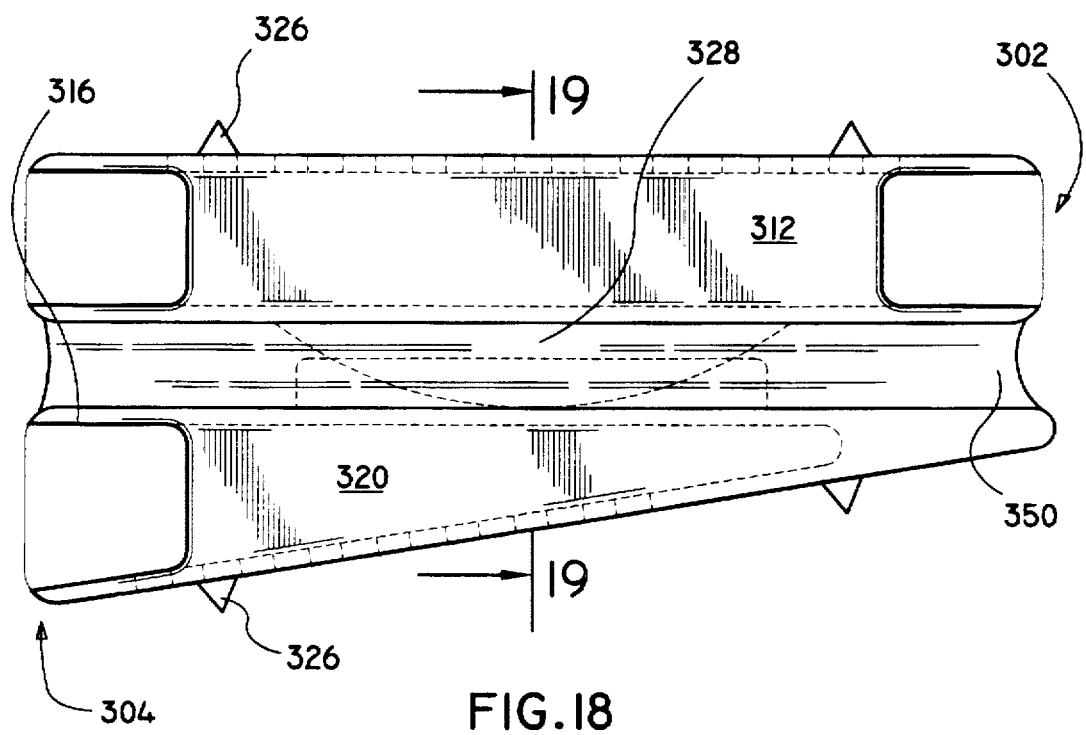
FIG. 18 is a side plan view of an alternate embodiment of the spinal implant of FIG. 12 incorporating a resilient layer disposed between the upper and lower support member.
Figure 19:
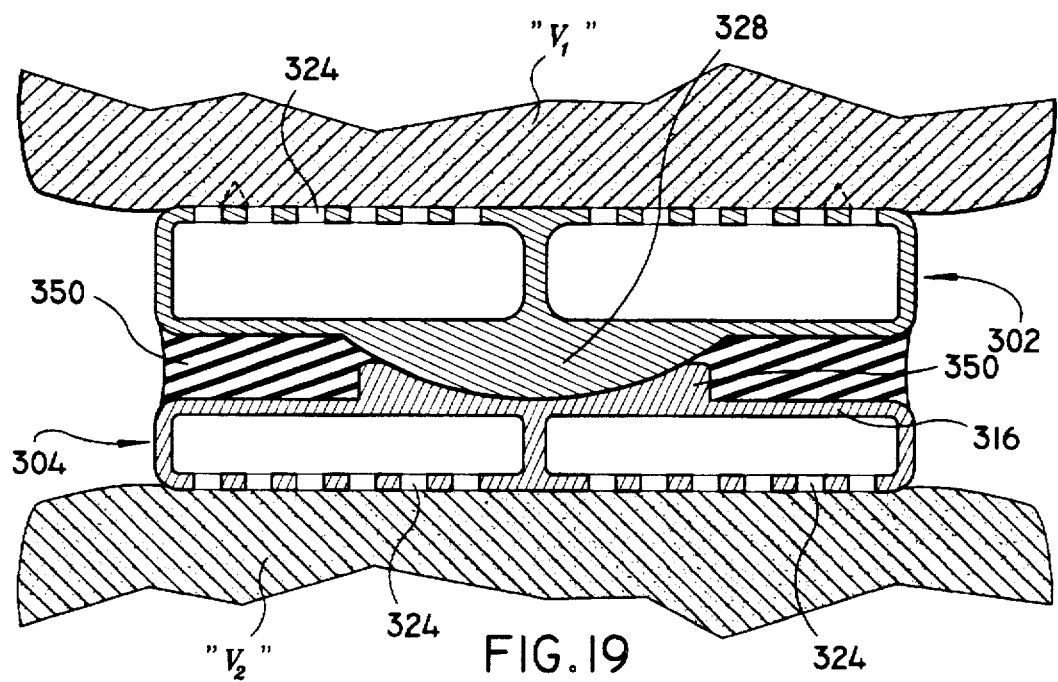
FIG. 19 is a sectional view illustrating the implant of FIG. 18 positioned within the intervertebral space.
Figure 20:
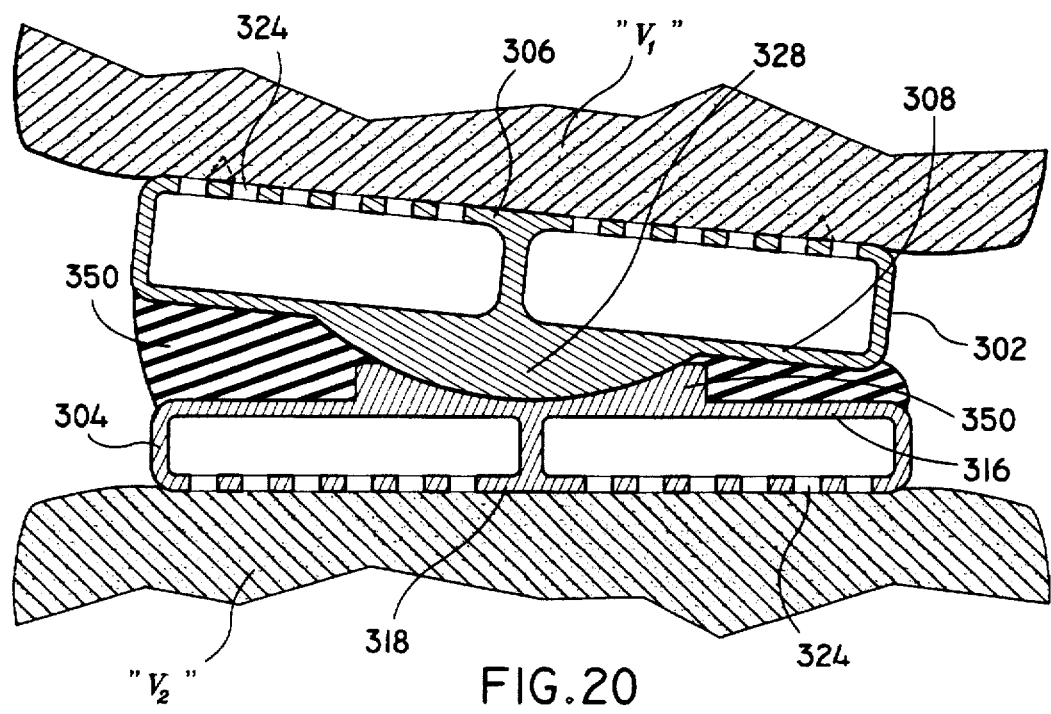
FIG. 20 is a view similar to the view of FIG. 19 illustrating articulating movement of the upper support member relative to the lower support member.
Figure 21:
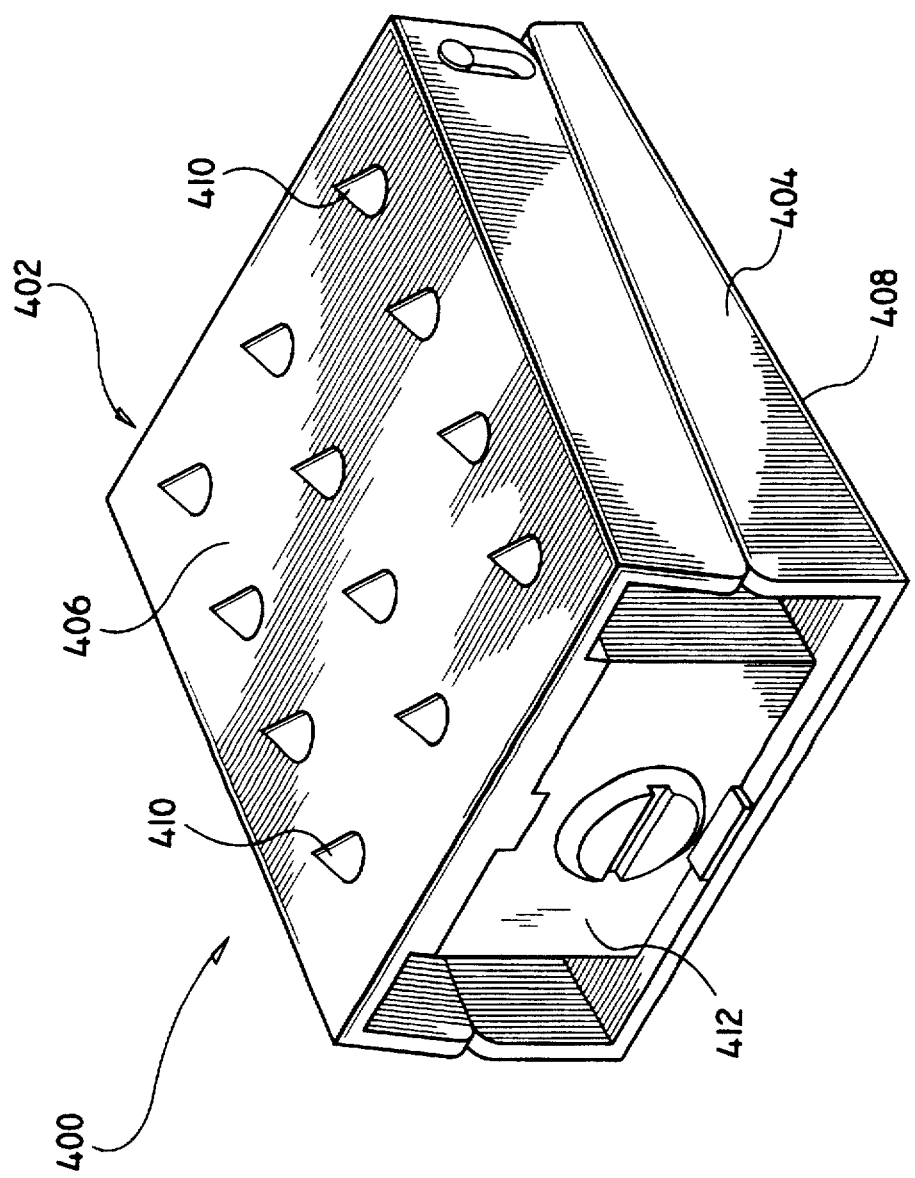
FIG. 21 is a perspective view of another alternate embodiment of the spinal implant.
Figure 22:
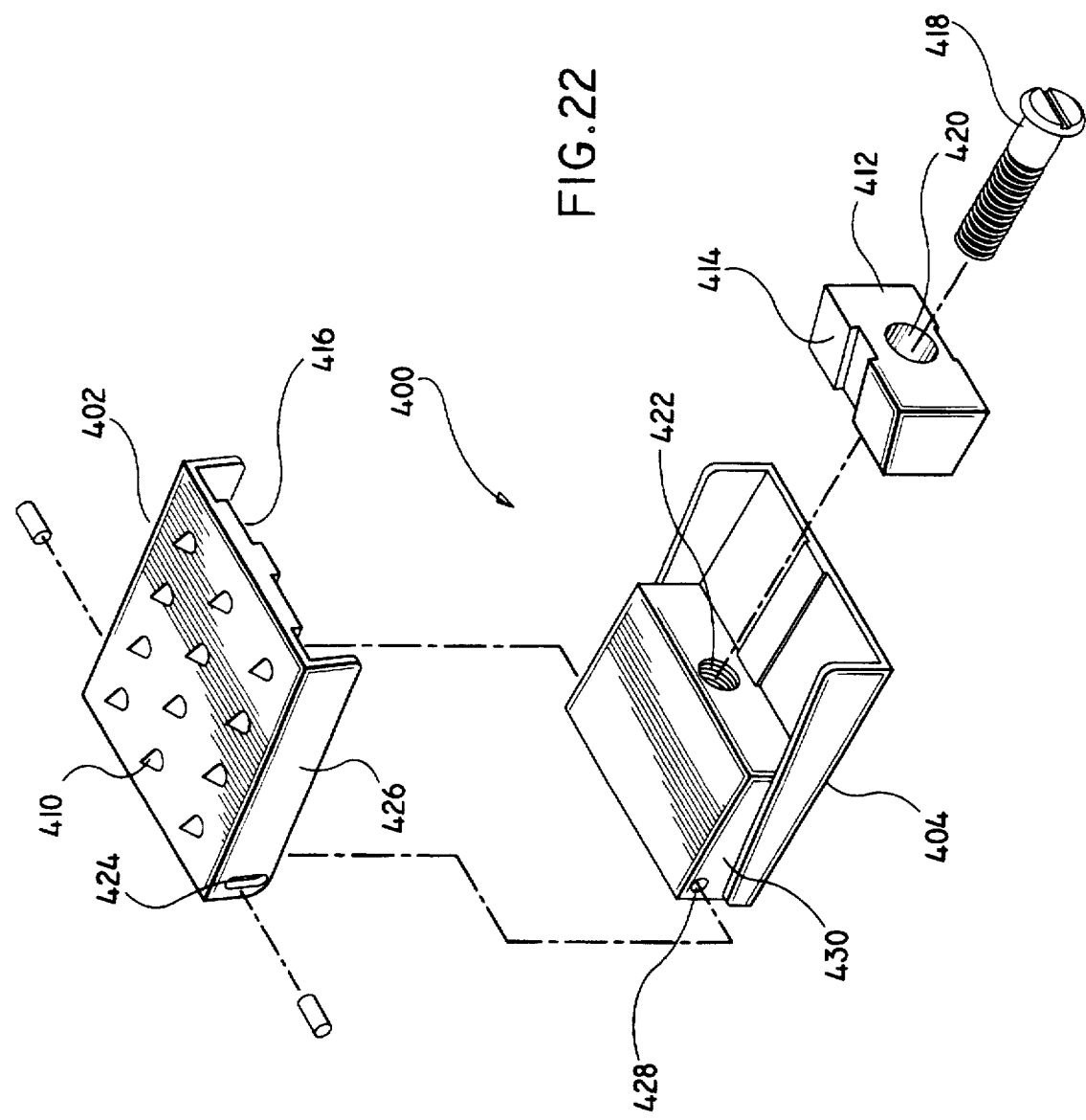
FIG. 22 is a perspective view with parts separated of the implant of FIG. 21 illustrating the upper and lower support members, and the camming mechanism disposed between the support members for selectively moving the first and second support members between a retracted position and an extended position.
Figure 25:
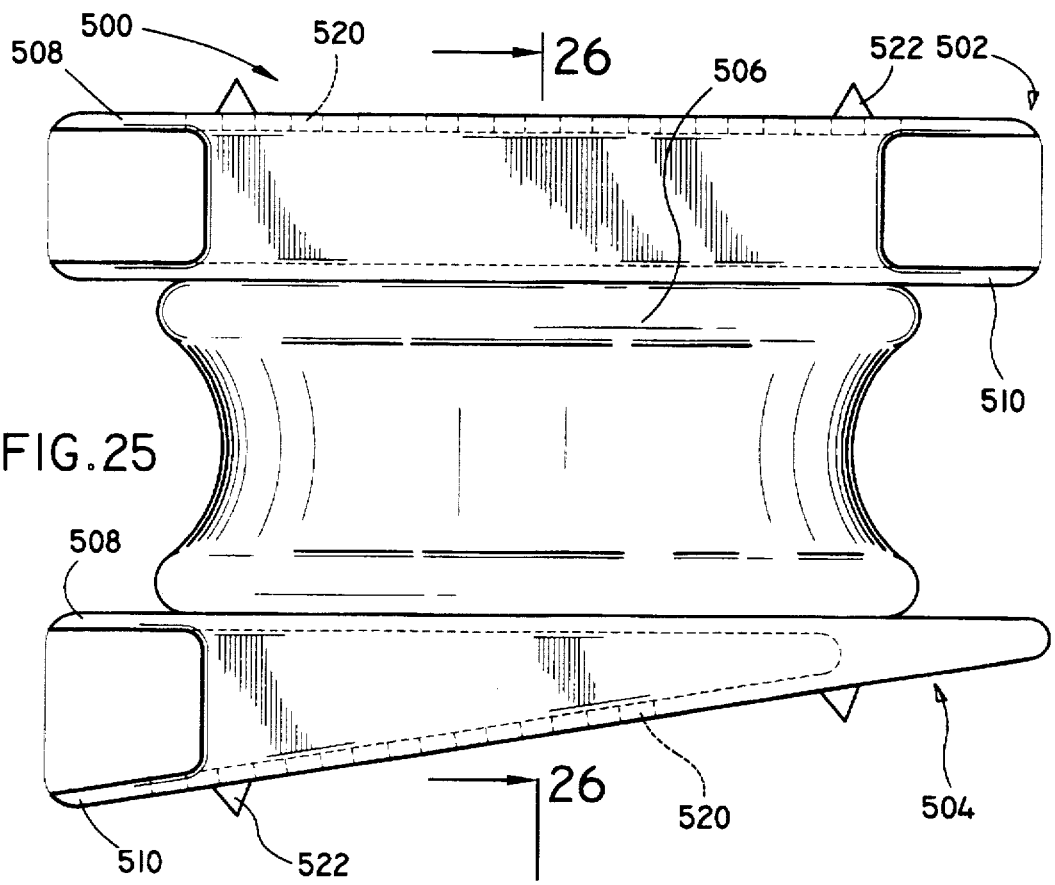
FIG. 25 is a side plan view of another alternate embodiment of the spinal implant.
Figure 26:
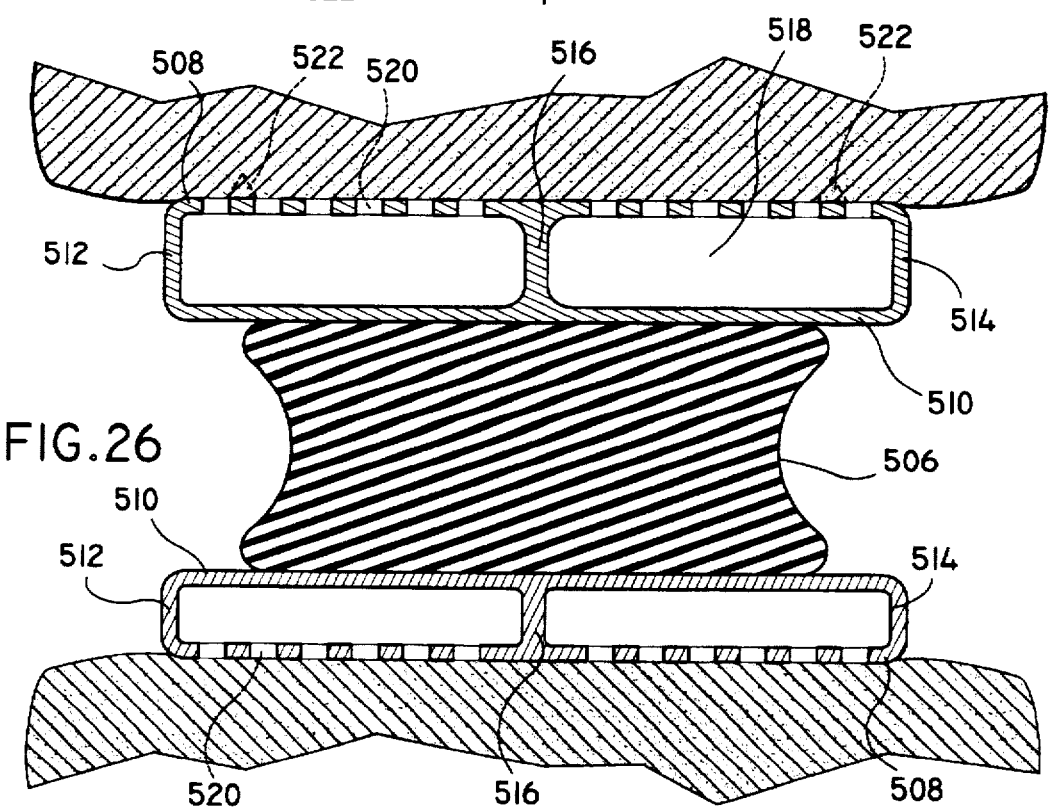
FIG. 26 is a cross-sectional view taken along the lines 26—26 of FIG. 25.

FIGS. 18–20 depict an alternate embodiment of the spinal implant 300 of FIGS. 12–17. This embodiment is similar in most respects to the implant 300, but, further incorporates a resilient layer 350 disposed between first and second support members 302, 304. Resilient layer 350 is preferably a sponge like material and serves to provide a cushion between first and second support members 302, 304 and the adjacent vertebrae "$V_1$, $V_2$" to accommodate compressive forces realized by the vertebral column during movement as depicted in FIG. 20.

Referring now to FIGS. 21–24, there is illustrated another alternate embodiment of the spinal implant of the present disclosure. Implant 400 includes two support members, i.e., upper support member 402 and lower support member 404 having respective contacting surfaces 406, 408. Each contacting surface 406, 408 has a plurality of pyramid-shaped projections 410 which facilitate engagement with the vertebral end plates of the adjacent vertebrae "$V_1$, $V_2$" upon insertion within the intervertebral space "i". Implant 400 further includes a camming arrangement for moving upper and lower support members 402, 404 between an open and a closed position. The preferred camming arrangement includes a camming block 412 which is adapted for traversing movement within the interior of implant 400. Camming block 412 defines an inclined camming surface 414 which engages a correspondingly dimensioned inner surface 416 of support member 402. The camming arrangement further includes a threaded element, e.g., screw 418, which traverses a bore 420 within camming block 412 and threadably engages an internal threaded bore 422 of lower support member 404.

Support members 402, 404 are interconnected through a pin and slot arrangement. More particularly, support member 402 has a pair of transversely extending slots 424 formed in side plates 426. Support member 404 has a pair of correspondingly positioned apertures 428 formed in side plates 430. A pin 432 traverses each slot and opening arrangement to connect upper support member 402 and lower support member 404.

FIGS. 23–24 illustrate rotational movement of screw 418 and the consequent corresponding traversing movement of camming block 412. In particular, rotation of screw 418 in a clockwise direction causes the screw to advance within threaded bore 422 thereby advancing camming block 412 in the direction indicated by the directional arrow in FIG. 24 and displacing upper support member 402 from lower support member 404. As upper support member 402 moves relative to lower support member 404, pins 432 traverse slots 424 of upper support member 402.

Referring now to FIGS. 25–28, another alternate embodiment of the present disclosure is illustrated. Implant 500 includes upper and lower support members 502, 504 and at a resilient layer 506 disposed between the support members 502, 504. Each support member 502, 504 includes first and second plate members 508, 510. First and second plate members 508, 510 are interconnected by peripheral interconnecting members 512, 514 and intermediate interconnecting member 516. An internal cavity 518 is defined between the plate members 508, 510. Support members 502, 504 are each preferably integrally formed to form a single component as shown.

First plate member 508 has a plurality of apertures 520 extending therethrough in communication with internal cavity 518 to promote bone ingrowth to facilitate the fusion process. A plurality of triangular-shaped projections 522 or teeth extend from the first plate member 508 and are dimensioned to penetrate the vertebral end faces to facilitate retention of the implant 500 within the intervertebral space. First plate member 510 of support member 504 is preferably inclined relative to axis "a" of the implant. This inclined configuration provides.

Figure 27:
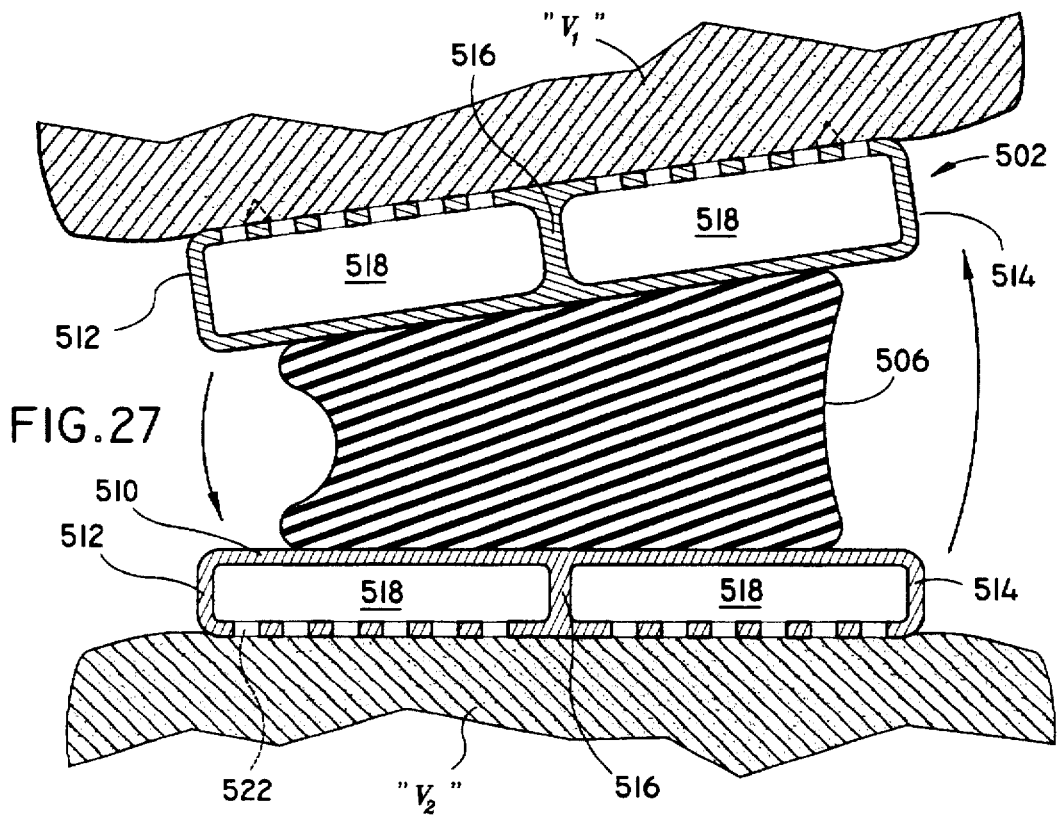
FIGS. 27–28 are views similar to the view of FIG. 26 illustrating adjusting motion of the implant during flexural movement of the vertebral column.
Figure 28:
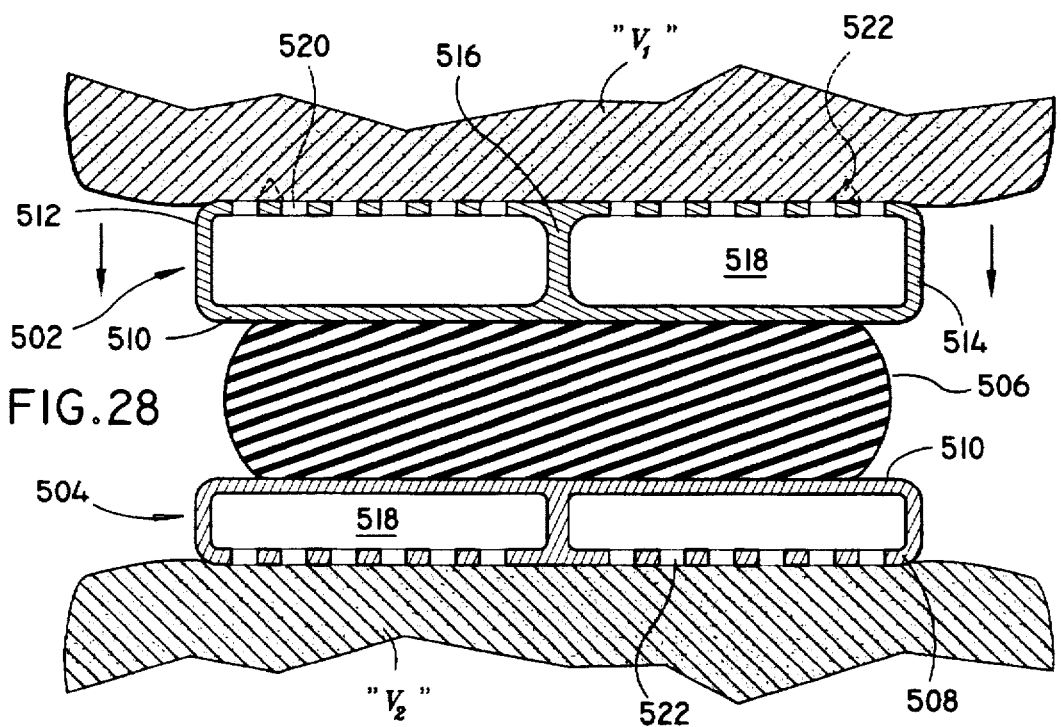

Resilient layer 506 disposed between plate members 508, 510 is preferably formed of a resilient material such as synthetic rubber or other elastomeric material. Resilient layer 506 provides sufficient forces to maintain the adjacent vertebrae in spaced relation while permitting relative flexural compressive movement of the vertebral column as depicted in FIGS. 27–28. Alternately, instead of resilient layer 506, compression springs, covered by a flexible film so as not to interfere with surrounding tissue, could be positioned between the upper and lower support member. Parallel pins to provide shear strength can be positioned adjacent the springs spanning the space between the upper and lower supports.

While the above description contains many specifics, these specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. An implant for insertion within an intervertebral space defined between adjacent vertebrae for supporting the vertebrae in predetermined spaced relation during healing which comprises at least first and second supporting members dimensioned for insertion within the intervertebral space, each supporting member including inner and outer plates arranged in spaced relation to define an internal cavity therebetween, each outer plate of the supporting members having contacting surfaces for contacting vertebral surfaces of the adjacent vertebrae and at least one aperture extending therethrough in communication with the respective internal cavity to permit bone ingrowth, the inner plate of the first supporting member having an arcuate articulating surface cooperating with a correspondingly dimensioned arcuate articulating surface of the inner plate of the second supporting member to permit articulating movement of the first supporting member to accommodate movement of the vertebral column during healing.

2. The implant according to claim 1 wherein the outer plates of the first and second supporting members each include a plurality of apertures to permit bone ingrowth.

3. The implant according to claim 1 wherein the articulating surfaces of the first and second supporting members each define a constant radius of curvature, the radius of curvature of each articulating surface being substantially equal.

4. The implant according to claim 1 further including a resilient member disposed between the first and second supporting members.

5. The implant according to claim 4 wherein the resilient member includes a layer of sponge-like material.

6. The implant according to claim 1 including bone growth inducing substances disposed within the internal cavity of each supporting member.

7. The implant according to claim 1 wherein the contacting surfaces of the outer plates have discontinuities to engage the vertebral surfaces of the adjacent vertebrae.

8. The implant according to claim 7 wherein the discontinuities are projections dimensioned for penetrating the vertebral surfaces of the adjacent vertebrae.

9. The implant according to claim 1 wherein the outer and inner plates of one of the first and second supporting members are in diverging relation to accommodate the natural lordosis of the vertebral column.

10. An implant for insertion between adjacent vertebrae, which comprises an implant member including upper and lower support components operatively connected to each other and arranged to span the intervertebral space to support the adjacent vertebrae in desired predetermined spaced relation during healing, each support component including outer and inner members arranged to define an internal cavity therebetween for accommodating bone growth inducing substances, the outer members of the support components having a plurality of apertures extending therethrough in communication with the internal cavity to promote bone ingrowth.

11. The implant according to claim 10 including bone growth inducing substances disposed within the internal cavity of each supporting component.

12. The implant according to claim 10 wherein the outer members of the upper and lower support components have discontinuities to engage the surfaces adjacent vertebrae.

13. The implant according to claim 12 wherein the discontinuities are projections dimensioned for penetrating the adjacent vertebrae.

14. The implant according to claim 12 wherein the inner members of the upper and lower support components have cooperating articulating surfaces to permit relative articulating movement of the upper and lower support components.

15. The implant according to claim 14 wherein the articulating surfaces of the upper and lower support components are generally arcuate in configuration.

16. The implant according to claim 14 including a resilient member disposed between the upper and lower support components and configured to support the adjacent vertebrae in spaced relation during healing while permitting relative movement thereof to accommodate variation in load during flexural movement of the adjacent vertebrae.

17. The implant according to claim 10 wherein the outer and inner members of one of the upper and lower support components are in diverging relation to accommodate the normal lordosis of the vertebral column.

18. The implant according to claim 10 including a resilient member disposed between the upper and lower support components and configured to support the adjacent vertebrae in spaced relation during healing while permitting relative movement thereof to accommodate variation in load during flexural movement of the adjacent vertebrae.

\* \* \* \* \*